US 11,806,198 B2

(12) United States Patent
Anderson et al.

(10) Patent No.: US 11,806,198 B2
(45) Date of Patent: Nov. 7, 2023

(54) SURGICAL INSTRUMENTS AND METHODS OF CLEANING SURGICAL INSTRUMENTS

(71) Applicant: INTUITIVE SURGICAL OPERATIONS, INC., Sunnyvale, CA (US)

(72) Inventors: S. Christopher Anderson, San Francisco, CA (US); William J. Park, San Jose, CA (US); Denise Ponganis, Fremont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1076 days.

(21) Appl. No.: 16/432,390

(22) Filed: Jun. 5, 2019

(65) Prior Publication Data

US 2019/0282328 A1    Sep. 19, 2019

Related U.S. Application Data

(63) Continuation of application No. 14/911,973, filed as application No. PCT/US2014/050925 on Aug. 13, 2014, now abandoned.
(Continued)

(51) Int. Cl.
*A61B 90/70* (2016.01)
*A61B 1/015* (2006.01)
(Continued)

(52) U.S. Cl.
CPC .............. *A61B 90/70* (2016.02); *A61B 1/015* (2013.01); *A61M 39/1011* (2013.01);
(Continued)

(58) Field of Classification Search
CPC . A61B 1/00121; A61B 1/00128; A61B 1/015; A61B 1/12; A61B 1/121;
(Continued)

(56) References Cited

U.S. PATENT DOCUMENTS

| 4,938,933 A | 7/1990 | Perrot |
| 5,090,433 A | 2/1992 | Kamaga |

(Continued)

FOREIGN PATENT DOCUMENTS

| WO | WO-0151116 A2 | 7/2001 |
| WO | WO-2015020906 A1 | 2/2015 |

OTHER PUBLICATIONS

International Search Report and Written Opinion for Application No. PCT/US2014/050925, dated Nov. 21, 2014, 15 pages.
(Continued)

*Primary Examiner* — Shefali D Patel
(74) *Attorney, Agent, or Firm* — JONES ROBB, PLLC

(57) ABSTRACT

In accordance with at least one exemplary embodiment, a surgical instrument comprises a shaft comprising a distal end, a proximal end, and a wall extending from the distal end to the proximal end, the wall surrounding an interior of the shaft. A transmission housing is located at the proximal end of the shaft and the shaft is rotatably coupled to the transmission housing. An actuator in the transmission housing is operably coupled to actuate rotation of the shaft. A port accessible from an exterior of the transmission housing is configured to be fluidically coupled to a fluid supply. A manifold in the transmission housing comprises an inlet and an outlet, the inlet being in fluid communication with the port, the outlet being in fluid communication with the interior of the shaft at the proximal end of the shaft.

20 Claims, 17 Drawing Sheets

Related U.S. Application Data

(60) Provisional application No. 61/866,311, filed on Aug. 15, 2013, provisional application No. 61/866,315, filed on Aug. 15, 2013.

(51) Int. Cl.
| | | |
|---|---|---|
| *A61M 39/10* | (2006.01) | |
| *A61B 90/00* | (2016.01) | |
| *A61B 34/30* | (2016.01) | |
| *A61B 34/00* | (2016.01) | |
| *A61M 25/00* | (2006.01) | |

(52) U.S. Cl.
CPC ......... *A61M 39/1055* (2013.01); *A61B 34/30* (2016.02); *A61B 34/70* (2016.02); *A61B 90/361* (2016.02); *A61B 2090/0813* (2016.02); *A61M 25/007* (2013.01); *A61M 2025/0031* (2013.01); *A61M 2025/0034* (2013.01); *A61M 2039/1016* (2013.01)

(58) Field of Classification Search
CPC .................. A61B 1/125; A61B 1/126; A61B 2018/00172; A61B 2018/0091; A61B 2090/0813; A61B 2090/701; A61B 2218/002; A61B 2560/0406; A61B 90/70; A61M 2025/0019; A61M 2025/0031; A61M 2025/0034; A61M 2039/0018; A61M 2039/1016; A61M 2209/10; A61M 25/007; A61M 25/0082; A61M 25/0097; A61M 39/1011; A61M 39/1055
See application file for complete search history.

(56) References Cited

U.S. PATENT DOCUMENTS

| | | |
|---|---|---|
| 5,527,276 A | 6/1996 | Bruce |
| 5,531,687 A | 7/1996 | Snoke et al. |
| 5,621,830 A | 4/1997 | Lucey et al. |
| 5,840,060 A | 11/1998 | Beiser et al. |
| 5,921,256 A | 7/1999 | Barin |
| 6,669,679 B1 | 12/2003 | Savage et al. |
| 6,695,774 B2 | 2/2004 | Hale et al. |
| 6,749,560 B1 | 6/2004 | Konstorum et al. |
| 7,150,713 B2 | 12/2006 | Shener et al. |
| 7,241,263 B2 | 7/2007 | Boulais et al. |
| 7,597,662 B2 | 10/2009 | Litscher et al. |
| 7,758,497 B2 | 7/2010 | Hem et al. |
| 7,833,153 B2 | 11/2010 | Takeuchi et al. |
| 7,942,868 B2 | 5/2011 | Cooper et al. |
| 8,118,732 B2 | 2/2012 | Banik et al. |
| 8,475,362 B2 | 7/2013 | Sohn et al. |
| 8,545,515 B2 | 10/2013 | Prisco et al. |
| 10,864,048 B2 | 12/2020 | Holop et al. |
| 2001/0025134 A1 | 9/2001 | Bon et al. |
| 2003/0130565 A1 | 7/2003 | Muller |
| 2004/0064045 A1 | 4/2004 | Weston et al. |
| 2005/0043682 A1 | 2/2005 | Kucklick et al. |
| 2005/0197536 A1 | 9/2005 | Banik et al. |
| 2006/0252993 A1 | 11/2006 | Freed et al. |
| 2008/0065105 A1 | 3/2008 | Larkin et al. |
| 2011/0009699 A1 | 1/2011 | Slenker et al. |
| 2011/0152879 A1 | 6/2011 | Williams |
| 2011/0204621 A1* | 8/2011 | Whitaker ........... A61M 39/1011 285/305 |
| 2012/0010628 A1 | 1/2012 | Cooper et al. |
| 2013/0123805 A1 | 5/2013 | Park et al. |
| 2014/0135579 A1 | 5/2014 | Brichard et al. |
| 2014/0155758 A1 | 6/2014 | Brichard et al. |
| 2016/0193012 A1 | 7/2016 | Anderson et al. |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

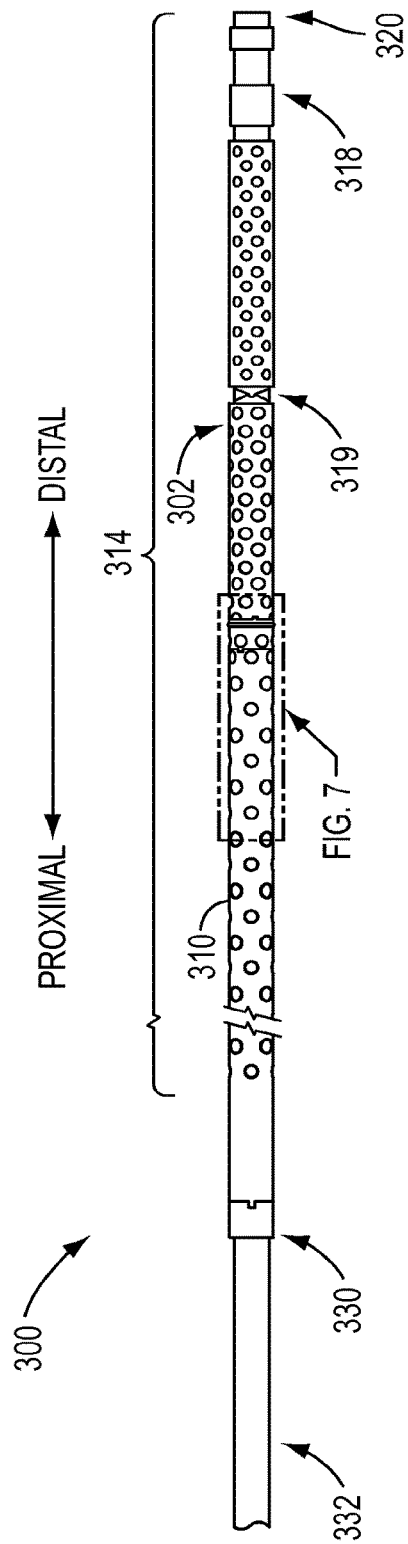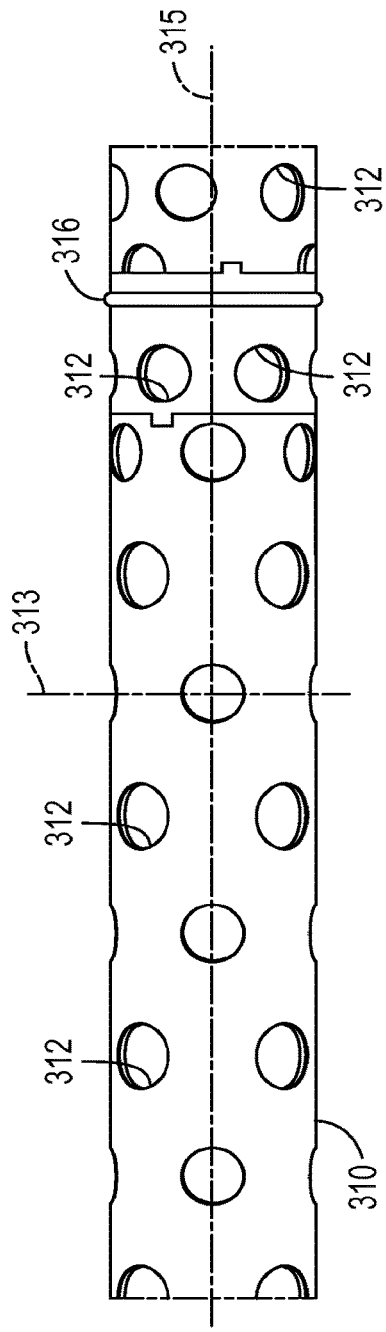
FIG. 6
FIG. 7

PROXIMAL ←——→ DISTAL

SURGICAL INSTRUMENTS AND METHODS OF CLEANING SURGICAL INSTRUMENTS

This application is a continuation application of application Ser. No. 14/911,973, filed Feb. 12, 2016, which is a national stage application of International PCT Application No. PCT/US2014/050925, filed internationally on Aug. 13, 2014, which claims the benefit of U.S. Provisional Application No. 61/866,311, filed Aug. 15, 2013 (now expired), and U.S. Provisional Application No. 61/866,315, filed Aug. 15, 2013 (now expired), each of which is hereby incorporated by reference herein in its entirety.

TECHNICAL FIELD

Aspects of the present disclosure relate to surgical instruments for a robotic surgical system and methods of cleaning surgical instruments.

BACKGROUND

Robotically controlled surgical instruments are often used in minimally invasive medical procedures (as used herein, the terms "robot" or "robotically" and the like include teleoperation or telerobotic aspects). During medical procedures, surgical instruments may be inserted within the body of a patient to perform medical procedures. During a medical procedure, surgical instruments may be exposed to various biomaterials, including fluids, tissues, and other materials. When it is desired to reuse a surgical instrument, or one or more components of a surgical instrument, it may be desirable to clean the instrument, or the one or more components of an instrument, in a manner that enables the instrument or components thereof to be reused safely. There exists a need for improvement of cleaning procedures and systems for surgical instruments to provide relative efficient and effective cleaning.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a surgical instrument comprises a shaft comprising a distal end, a proximal end, and a wall extending from the distal end to the proximal end, the wall surrounding an interior of the shaft. A transmission housing is located at the proximal end of the shaft and the shaft is rotatably coupled to the transmission housing. An actuator in the transmission housing is operably coupled to actuate rotation of the shaft. A port in the transmission housing is configured to be fluidically coupled to a fluid supply. A manifold in the transmission housing comprises an inlet and an outlet, the inlet being in fluid communication with the port, the outlet being in fluid communication with the interior of the shaft at the proximal end of the shaft. The fluid communication of the inlet with the port and the fluid communication of the outlet with the interior of the shaft are maintained through a range of rotational orientations of the shaft relative to the transmission housing.

In accordance with at least another exemplary embodiment, a surgical instrument comprises a transmission housing, and a shaft comprising a distal end, a proximal end, and a wall surrounding an interior of the shaft, the proximal end of the shaft being rotatably coupled to the transmission housing at a rotational coupling. The surgical instrument also comprises a fluid port in the transmission housing, a fluid connection locking mechanism coupled to the fluid port, and a fluid manifold in the transmission housing. The fluid manifold comprises an inlet and an outlet, the inlet being in fluid communication with the fluid port and the outlet being in fluid communication with the interior of the shaft at the proximal end of the shaft. The fluid communication of the manifold with the port and the interior of the shaft is independent of a rotational position of the shaft relative to the transmission housing.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

FIG. 6 is a partial side view of another exemplary embodiment of a surgical instrument according to the present disclosure.

FIG. 7 is the enlarged view labeled FIG. 7 in FIG. 6.

DETAILED DESCRIPTION

Figure 1:
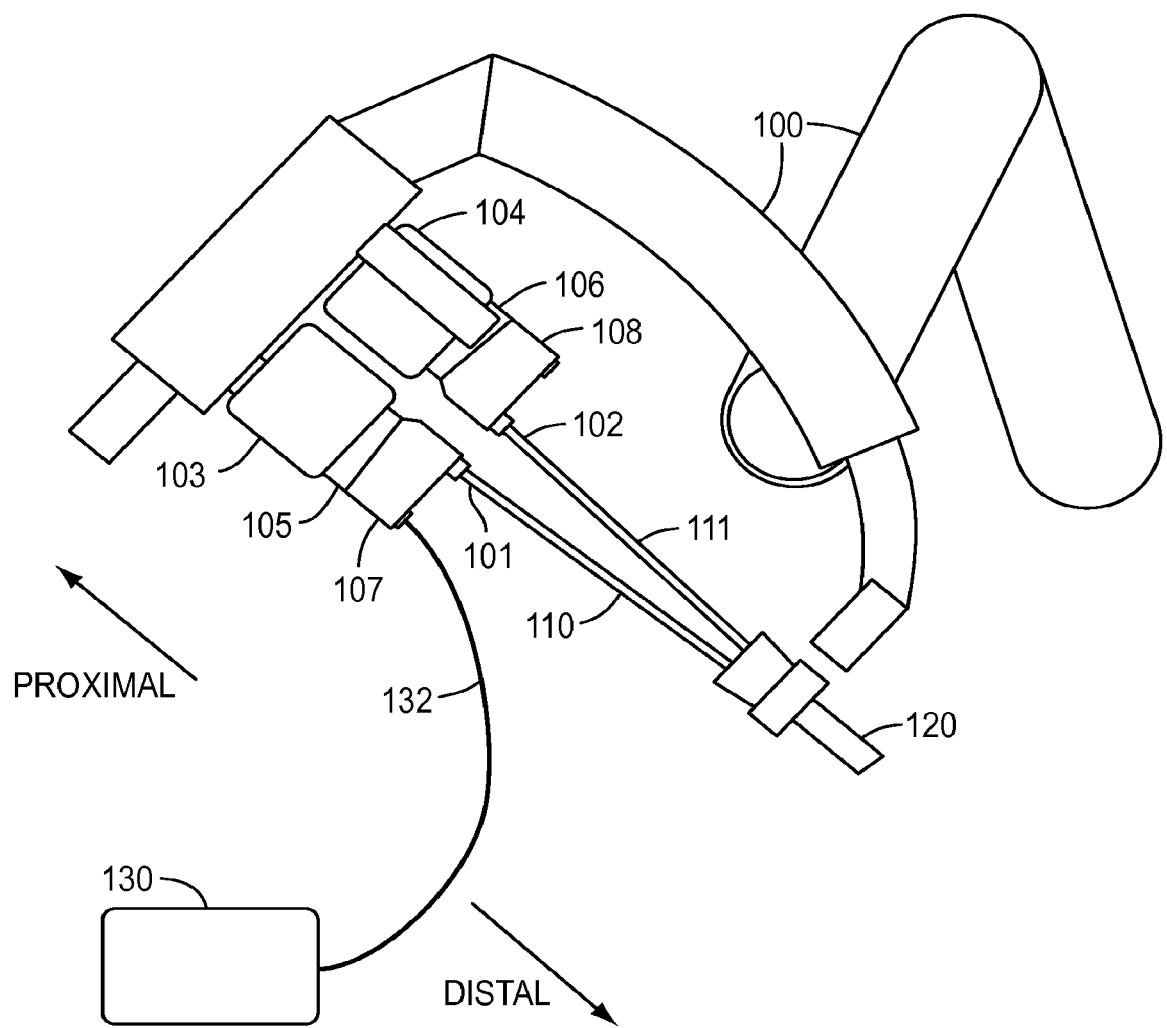
FIG. 1 is a partial schematic view of an exemplary embodiment of a manipulator arm of a patient side cart with two electrosurgical instruments in an installed position, one of which is shown in electrical communication with a flux generator.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. For instance, the manifold of the exemplary embodiment of FIG. 3 may be used with any of the surgical instruments described herein and the various exemplary embodiments of surgical devices of FIGS. 4-17 and 27-31 may be used with any combination of the exemplary embodiments of cleaning devices of FIGS. 18-26.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

In accordance with various exemplary embodiments, the present disclosure contemplates surgical instruments for robotic surgical systems that include features to facilitate cleaning of the surgical instruments. Further, the present disclosure contemplates devices, systems, and methods for cleaning surgical instruments or one or more components of a surgical instrument. For instance, the embodiments described herein may be used to remove material, such as, for example, biomaterial, from a surgical instrument or one or more components of a surgical instrument to facilitate reuse of the surgical instrument, for example, to enable the surgical instrument to perform multiple medical procedures on the same or differing patients. The exemplary embodiments described herein contemplate that at least a portion of a surgical instrument (including surgical instruments with an end effector and camera instruments) may have an open architecture that permits, for example, cleaning fluid to pass through an external wall of the instrument to access an interior of the instrument and remove material picked up by the instrument during a surgical procedure, such as biomaterial. In another instance, an open architecture may facilitate visual inspection of an interior of an instrument by permitting an observer to view the interior, such as through apertures in an outer wall of the instrument. Various exemplary embodiments further contemplate that a surgical instrument may include a proximal manifold to facilitate flushing of a cleaning fluid through an interior of the surgical instrument along its shaft from the proximal end toward a distal end.

Various exemplary cleaning devices to be used during a cleaning procedure of a surgical instrument are also contemplated. For instance, a cleaning fluid distribution device may be used to distribute cleaning fluid over a surgical instrument inserted into the device, such as by directing fluid with velocity to surgical instrument components to be cleaned. The instrument and cleaning fluid distribution device may be moved relative to one another. The cleaning fluid distribution device may advantageously permit cleaning of a surgical device in a relatively simple and efficient manner while reducing the potential for fluid being sprayed onto a user and with less waste of fluid, such as by providing a high fluid velocity to substantially remove material from an instrument. In another exemplary embodiment, a cleaning fluid routing device may be used to both route cleaning fluid around an exterior of a surgical instrument and to route cleaning fluid into an interior of the surgical instrument during a cleaning procedure. Further, the exemplary embodiments of surgical instruments and cleaning devices described herein may permit cleaning of surgical instruments with ordinary water without the use of detergents, although detergents and other cleaning solutions may be used to clean surgical instruments.

Referring now to the schematic illustration of FIG. 1, a portion of an exemplary embodiment of a manipulator arm 100 of a patient side cart with two surgical instruments 101, 102 in an installed position is shown. A teleoperated robotic surgical system, including a patient side cart comprising manipulator arm 100, may be configured according to the exemplary embodiments described in U.S. patent application Ser. No. 14/070,184, filed Nov. 1, 2013 (for "FLUX DISAMBIGUATION FOR TELEOPERATED SURGICAL SYSTEMS"), which is incorporated by reference herein. The schematic illustration of FIG. 1 depicts only two surgical instruments for simplicity, but more than two surgical instruments may be received in an installed position at a patient side cart as those having ordinary skill in the art are familiar with. Each surgical instrument 101, 102 includes an instrument shaft 110, 111 that at a distal end has a moveable end effector (discussed below in regard to FIG. 2) or a camera or other sensing device, and may or may not include a wrist mechanism (discussed below in regard to FIG. 2) to control the movement of the distal end.

In the exemplary embodiment of FIG. 1, the distal end portions of the surgical instruments 101, 102 are received through a single port structure 120 to be introduced into the patient. Other configurations of patient side carts that can be used in conjunction with the present disclosure can use several individual manipulator arms. In addition, individual manipulator arms may include a single instrument or a plurality of instrument. Further, an instrument may be a surgical instrument with an end effector or may be a camera instrument or other sensing instrument utilized during a surgical procedure to provide information, (e.g., visualization, electrophysiological activity, pressure, fluid flow, and/or other sensed data) of a remote surgical site.

Force transmission mechanisms 107, 108 are disposed at a proximal end of each shaft 110, 111 and connect through a sterile adaptor 105, 106 with actuation interface assemblies 103, 104. Actuation interface assemblies 103, 104 contain a variety of mechanisms (discussed further below with regard to the exemplary embodiment of FIG. 2) that are controlled by a controller (e.g., at a control cart of a surgical system) to respond to input commands at a surgeon side console of a surgical system to transmit forces to the force transmission mechanisms 107, 108 to actuate instruments 101, 102. The diameter or diameters of an instrument shaft, wrist mechanism, and end effector are generally selected according to the size of the cannula with which the instrument will be used and depending on the surgical procedures being performed. In various exemplary embodiments, a shaft and/or wrist mechanism about 4 mm, 5 mm, or 8 mm in diameter, for example, to match the sizes of some existing cannula systems. According to an exemplary embodiment, one or more of surgical instruments 101, 102 may be in communication with a flux source 130 via a flux transmission conduit 132. For example, if a surgical instrument 101 is an electrosurgical instrument, flux transmission conduit 132 is an electrical energy transmission cable and flux source 130 is an electrical energy generator.

In accordance with various exemplary embodiments, a surgical instrument for a robotic surgical system may include features to facilitate cleaning of the instrument. For instance, at least a portion of a surgical instrument may have an open architecture. An open architecture may permit, for example, cleaning fluid to pass through an external wall of the instrument to access an interior of the instrument and remove material picked up by the instrument during a surgical procedure, such as biomaterial. In another instance, an open architecture may facilitate visual inspection of an interior of an instrument by permitting an observer to view the interior, such as through apertures in an outer wall of the instrument. Further, an instrument may include a manifold and a port to flush fluid through an interior of the instrument.

Surgical Instruments with Flushing Manifolds

Figure 2:
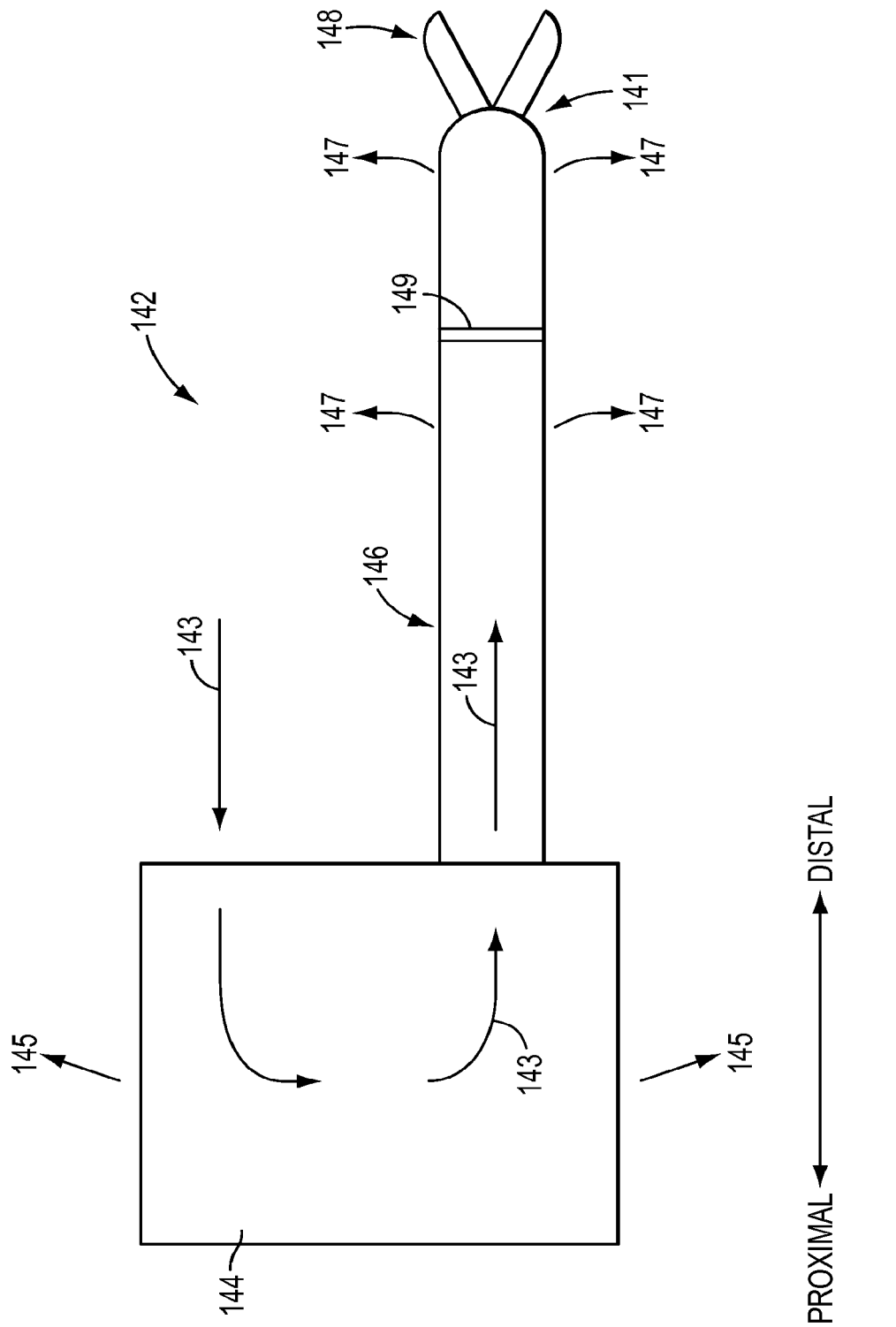
FIG. 2 is a cross-sectional side view of an exemplary embodiment of a surgical instrument according to the present disclosure.

With reference to FIG. 2, a cross-sectional side view of surgical instrument 142 is shown, according to an exemplary embodiment. Surgical instrument 142 may include a proximal portion 144 and a shaft 146. Surgical instrument 142 may be a therapeutic instrument and may include an end effector 148 for performing a surgical procedure, which may be supported from a distal end of the surgical instrument shaft 146, as shown in the exemplary embodiment of FIG. 2. However, as above, surgical instrument 142 is not limited to a therapeutic instrument having an end effector, but also may also include endoscopic camera or other sensing instruments, an example of which is shown and described further below. Proximal portion 144 may include a force transmission mechanism to actuate surgical instrument 142, as described above in regard to the exemplary embodiment of FIG. 1. According to an exemplary embodiment, a seal 149 may be provided within shaft 146, such as to minimize or prevent material that instrument 142 is exposed to during a surgical procedure from moving from distal end 141 of instrument 142 towards proximal portion 144. Seal 149 may be made of, for example, silicone. Seal 149 may be located a distance from distal end 141, such as proximal to a wrist or other bendable portion (not shown in FIG. 2) of instrument 142. Further, if instrument includes a joggle joint, not shown in FIG. 2 but discussed further below, seal 149 may be located proximal to the joggle joint.

According to an exemplary embodiment, seal 149 may seal against actuation members that extend from proximal portion 144 through shaft 146 to distal end 141, such as to actuate end effector 148. According to an exemplary embodiment, an actuation member may have a composite structure that includes a rigid portion extending through shaft 146 and through seal 149 and a flexible portion that extends through joints or other bendable instrument portions distal to seal 149, such as a wrist and/or joggle joint, for example. The rigid portion of the actuation member may be a rigid rod or tube and the flexible portion may be a cable passing through a hollow interior of the rigid portion. The cable may be connected to the rigid portion, such as via crimping. The rigid portion may have a substantially smooth outer surface that seals well with an aperture through seal 149. The rigid portion may be a tube made of metal, such as, for example, stainless steel. In another example, the rigid portion may be a tube comprising a composite material, such as, for example, a composite polymer material.

Seal 149 may also function as a pressure seal to minimize or prevent flow of fluid through the interior of shaft 146 from distal end 141 to proximal portion 144, such as when an interior of a patient is insufflated during a surgical procedure, according to an exemplary embodiment. According to an exemplary embodiment, instrument 142 may include a sheath (not shown) over at least a portion of shaft 146. A sheath may facilitate minimizing or preventing a flow of fluid between an interior of shaft 146 and an exterior of shaft 146, such as when at least a portion of shaft 146 includes an open architecture, which will be discussed below. A positive pressure used during insufflation may be, for example, about 0.25 psi. Permitting insufflation fluid to escape at excessive levels from within a patient may cause drying of tissue within the patient, but seal 149 may minimize or prevent drying from occurring by minimizing to an acceptable level escaping gases.

According to an exemplary embodiment, a cleaning procedure for a surgical instrument may include irrigating a surgical instrument with a fluid. As will be described below, irrigating a surgical instrument may include supplying fluid to an exterior and/or interior of the surgical instrument in various manners, including but not limited to, for example, spraying, flushing, and/or soaking. An interior of the surgical instrument may be irrigated, for example, by introducing fluid into the surgical instrument from an end of the instrument and/or via fluid entering an interior of the shaft through an open architecture of the shaft. According to an exemplary embodiment, cleaning fluid 143 may be introduced into proximal portion 144 of surgical instrument 142, as shown in FIG. 2. At least a portion 145 of cleaning fluid 143 may be permitted to flow through and out of proximal portion 144 to irrigate proximal portion 144. Cleaning fluid 143 may continue to flow into an interior of the shaft 146 to flush the interior of shaft 146. According to an exemplary embodiment, surgical instrument 142 may include an open architecture (not shown but described further below in various exemplary embodiments) to facilitate cleaning of instrument 142. The open architecture may, for example, permit cleaning fluid 143 within shaft 146 to exit shaft 146, as shown by fluid portions 147, to facilitate flushing of shaft 146. When seal 149 is present within shaft 146, fluid 143 may be prevented from flowing in a proximal-to-distal direction past seal 149 and be forced to exit shaft 146 as fluid portions 147. However, seal 149 may be absent or seal 149 may be configured during a cleaning procedure to permit at least a portion of fluid 143 to flow past seal 149 in the proximal-to-distal direction towards distal end 141 and exit shaft 146 as fluid portions 147.

Figure 3:
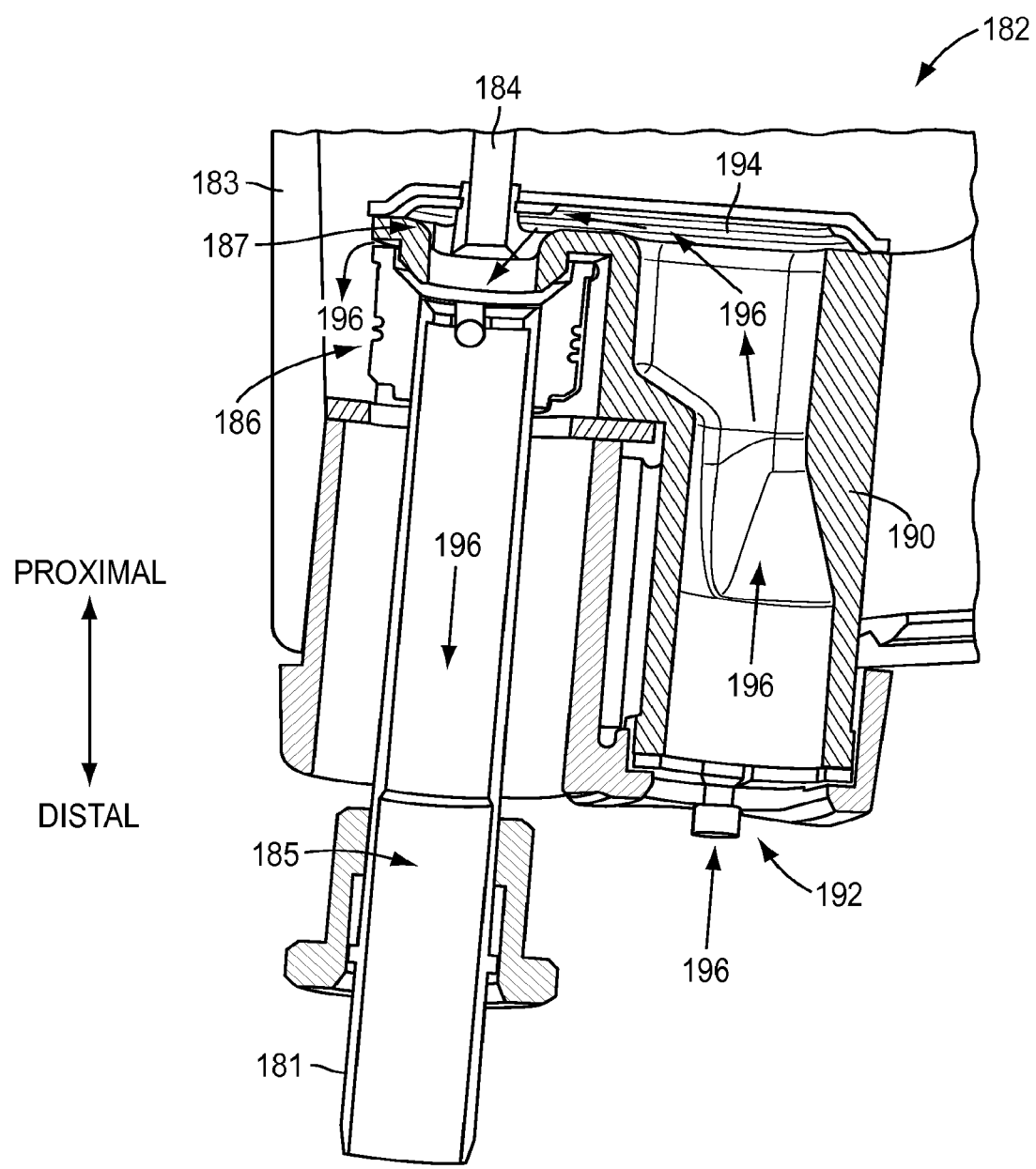
FIG. 3 is a partial cross-sectional view of an exemplary embodiment of a proximal portion of a surgical instrument in accordance with the present disclosure.

Turning to FIG. 3, a cross-sectional view of a proximal portion 182 of a surgical instrument is shown. The instrument includes a shaft 181 and a transmission housing 183 connected to a proximal end of shaft 181. According to an exemplary embodiment, an end effector actuator 184 (a partial view of which is shown) may be provided to actuate an end effector (not shown) of instrument. End effector actuator 184 may be, for example, one or more of a push/pull rod member, pull-pull tension members, or other mechanisms recognized by one of ordinary skill in the art to actuate an end effector of a surgical instrument. Proximal portion 182 may further include an actuator 186 to rotate shaft 181, such as, for example, a capstan or other device recognized by one of ordinary skill in the art to rotate an instrument shaft.

As shown in the exemplary embodiment of FIG. 3, the transmission housing 183 may include a manifold 190 to receive fluid and direct the fluid into at least one of an interior of housing 183 and an interior 185 of shaft 181. Because manifold 190 may be located in transmission housing 183 in a proximal portion of an instrument, manifold 190 may be located in a portion of instrument that does not contact a patient during a surgical procedure. Thus, although manifold 190 and its associated components may not become soiled during a surgical procedure, manifold 190 and its associated components may assist with cleaning an instrument. A portion of manifold 190, such as a proximal portion 194 of manifold 190, may be removable to permit access to an interior of manifold 190 and shaft 181. According to an exemplary embodiment, portion 194 may be sealed to a remainder of manifold 190. Actuator 184 may extend through portion 194 via a sealed aperture or connection 187, such as, for example, a sealed bushing.

As shown in the exemplary embodiment of FIG. 3, manifold 190 may include a port 192 to receive fluid. Port 192 may be, for example, an aperture, fitting, or connection configured to connect a supply of fluid to manifold 190. For instance, port 192 may be configured to connect with a tube or hose supplying fluid for a cleaning procedure, for example, from a faucet (which may be connected to a pressure regulator) or other source; alternatively, the port 192 can be configured to connect directly to a faucet. Although cleaning procedures according to the exemplary embodiments discussed herein may be conducted by hand, such as by a technician conducting a cleaning procedure, the exemplary embodiments are not limited to manual reprocessing or cleaning procedures. According to an exemplary embodiment, the exemplary embodiments described herein may be used with an automated reprocessing apparatus or method, such as in the exemplary embodiments of International Application No. PCT/US14/49454, filed on Aug. 1, 2014 (for "DEVICES, SYSTEMS, AND METHODS FOR SURGICAL INSTRUMENT REPROCESSING), which is hereby incorporated by reference herein in its entirety.

According to an exemplary embodiment, port 192 may include a locking feature that locks a connection, such as a tube or hose, to port 192 so that the connection may only be disconnected by actuating a release mechanism of the port 192, such as a button or lever. The locking feature may permit the connection to remain in place, even when high cleaning fluid pressures are used, which may cause other non-locking fittings to loosen and even disconnect.

Figure 27:
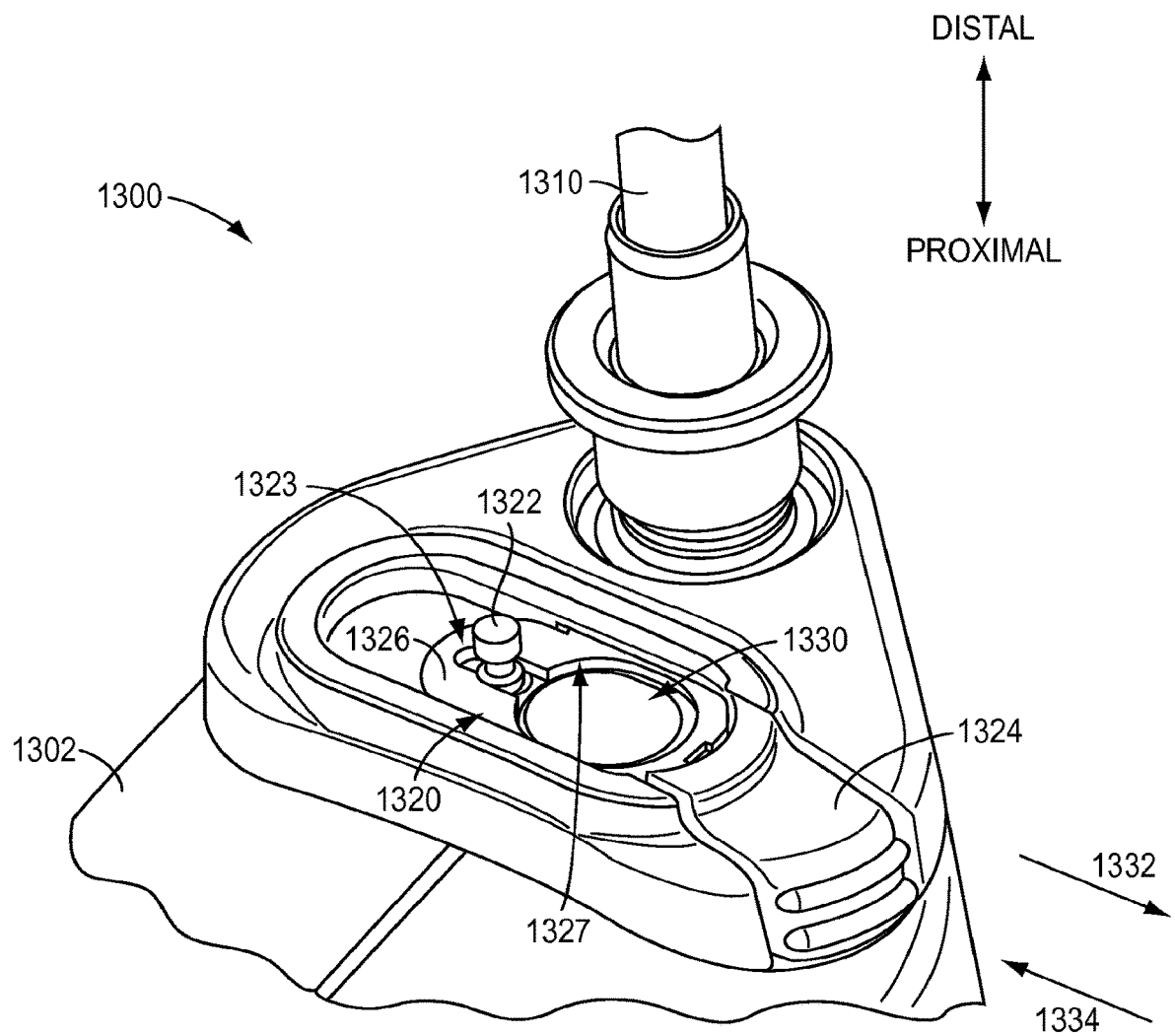
FIG. 27 is partial perspective view of an exemplary embodiment of a proximal portion of a surgical instrument with a locking mechanism in accordance with the present disclosure.

Turning to FIG. 27, a proximal portion 1300 of a surgical instrument is shown, similar to the exemplary embodiment of FIG. 3. For instance, proximal portion 1300 may include a transmission housing 1302, similar to housing 183 of the exemplary embodiment of FIG. 3, connected to a proximal end of an instrument shaft 1310. Proximal portion 1300 further includes a locking mechanism 1320 to lock a connection to a port 1330 of proximal portion 1300. Locking mechanism 1320 may permit the connection to remain in place and connected to port 1330, even when fluid at high pressure is used. According to an exemplary embodiment, locking mechanism 1320 includes a plate 1326 located at port 1330. Plate 1326 may be biased to a locking position so that an edge 1327 forming an aperture through plate 1326 is offset from port 1330. For instance, plate 1326 may be biased in direction 1332, such as by a spring or other biasing member. A pin 1322 may be provided with a slot 1323 of plate 1326 to limit the distance plate 1326 is biased along direction 1332, according to an exemplary embodiment.

When a connection is made with port 1330, the connection may be inserted into the aperture formed by edge 1327 of plate 1326. Because the aperture formed by edge 1327 is offset from port 1330 when plate 1326 is biased into the locking position, forcing the connection into the aperture may overcome the biasing force. For instance, inserting the connection may force plate to move along direction 1334, causing aperture formed by edge 1327 to substantially align with port 1330 so that the connection may be fully inserted into port 1330. Once the connection is fully inserted into port 1330, plate 1326 may once again be biased to the locking position, such as in direction 1332. According to an exemplary embodiment, when plate 1326 is biased to the locking position when a connection has been inserted into port 1330, edge 1327 of plate 1326 may be inserted into a corresponding groove or depression (not shown) of connection to substantially lock connection to port 1330. As a result, the attachment between connection and port 1330 may resist the force of high pressure fluid and remain in place during a cleaning procedure. Further, the connection may be simply released when a cleaning procedure is complete by pressing plate 1326 to overcome the biasing force. For instance, a release portion 1324 of plate 1326 may be pressed to move plate 1326 in direction 1334, which may disengage edge 1327 from the corresponding groove or depression of the connection, causing the connection to be released from port 1330. As shown in the exemplary embodiment of FIG. 3, fluid 196 may flow in the direction indicated by arrows by first entering port 192 and into manifold 190. According to an exemplary embodiment, at least a portion of fluid 196 may be used to irrigate housing 183. The portion of fluid 196 used to irrigate housing 183 may be, for example, up to about one third of the fluid 196 that enters port 192. A portion of fluid 196 may be permitted to exit manifold 190, such as through one or more gaps between actuator 186 and manifold 190, to irrigate an interior of housing 183. Fluid 196 may subsequently exit housing 183, such as by exiting unsealed gaps between members forming housing 183, such as between clamshell members forming housing 183.

According to an exemplary embodiment, at least a portion of fluid 196 may flow into an interior 185 of shaft 181, as shown in FIG. 3. According to an exemplary embodiment, manifold 190 may be configured to change the direction of fluid flow to direct fluid 196 into shaft interior 185. For instance, manifold 190 may be configured to change the direction of fluid flow substantially 180 degrees between the entry of fluid into port 192 and the entry of fluid into interior 185 of shaft 181, although other flow paths and changes of direction may be implemented in manifold 190.

According to an exemplary embodiment, manifold 190 may be configured to receive various fluids. For instance, manifold 190, including port 192, may be configured to receive a liquid to flush through a surgical instrument during a cleaning procedure. A liquid may include, for example, water (e.g., tap water) or a water solution, such as a mixture of water and a detergent. In another instance, manifold 190, including port 192, may be configured to receive a gas. A gas, such as, for example, air, may be flushed through an interior of a surgical instrument to check components of the surgical instrument for leaks, such as punctures in a sheath of a surgical instrument.

Surgical Instruments with Open Architectures

According to various exemplary embodiments, non-jointed shaft portions of an instrument may have an open architecture. A portion of an instrument shaft having a tubular wall extending along a longitudinal axis of the instrument may have an open architecture by including a plurality of holes through and along the exterior of the tubular wall, according to an exemplary embodiment. According to an exemplary embodiment, an open architecture may include shaft portions having a plurality of holes arranged in a pattern that repeats in both an axial direction and a radial direction along at least a portion of the length of the shaft of a surgical instrument. According to another exemplary embodiment, an open architecture may be a non-jointed shaft portion having a total area of holes that is greater than a total area of solid areas of the shaft portion that lacks holes. Although portions of a surgical instrument shaft having an open architecture may be non-jointed, such portions may extend on each side of a joint in a proximal-distal direction of the shaft. Thus, although joints may be depicted in accompanying drawings as being located in portions having an open architecture, joints may lack an open architecture according to the exemplary embodiments described above. However, an open architecture is not limited to non-jointed shaft portions and joints themselves may include an open architecture, such as by providing apertures that provide fluid communication between an exterior of an instrument and an interior of an instrument.

Figure 4:
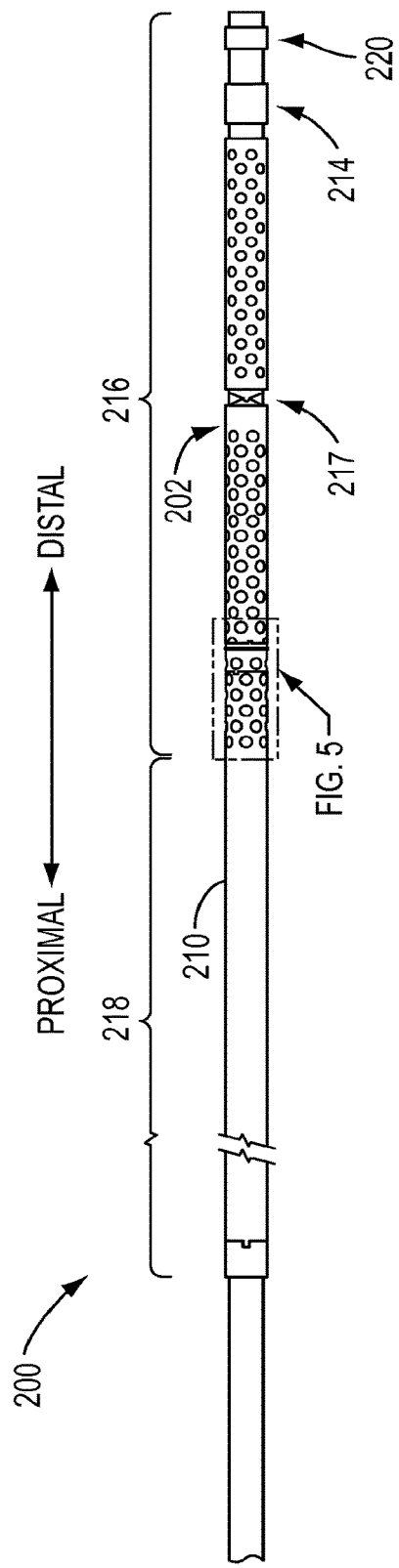
FIG. 4 is a partial side view of an exemplary embodiment of a surgical instrument according to the present disclosure.
Figure 5:
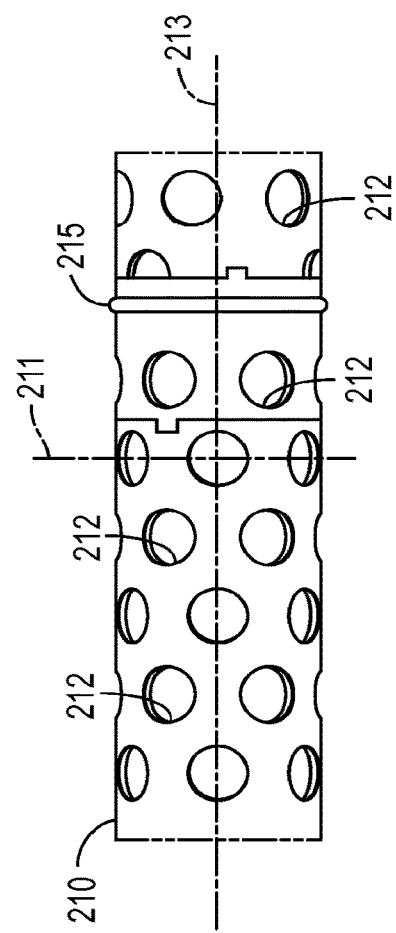
FIG. 5 is the enlarged view labeled FIG. 5 in FIG. 4.

Turning to FIG. 4, an exemplary embodiment of a shaft 200 of a surgical instrument is shown. Shaft 200 may include a plurality of holes 212 through a wall 210 of shaft 200 (see enlarged view in FIG. 5), with holes 212 providing flow communication between an interior of instrument and a surrounding environment exterior to the wall 210. As shown in FIG. 5, for example, the plurality of holes 212 in a portion of the shaft having an open architecture may be arranged so that at least one transverse cross-sectional plane 211 and at least one longitudinal cross-section plane 213 each intersect multiple holes 212. Holes 212 are not limited to the configuration shown in FIG. 5 and may instead, for example, be arranged in random orientation so that adjacent holes 212 are not aligned in longitudinal and/or transverse planes, such as planes 211 and/or 213 of the exemplary embodiment of FIG. 5. Shaft wall 210 can provide an exterior surface of shaft 200 when shaft 200 does not include a sheath overlaying the shaft; otherwise a sheath may cover at least a portion of the wall 210, such as portion that includes holes 212. For example, during a surgical procedure, a sheath (not shown) may be disposed to cover a distal end portion of the shaft from a location proximal to joint 217 to a distal end portion of the instrument, including a wrist 214, if any, such that the end effector extends past the sheath. Those having ordinary skill in the art are familiar with such sheaths for surgical instruments. Shaft 200 may include one or more features to engage with and/or seal with a sheath, such as a protrusion 215 shown in the enlarged view of FIG. 5. Such features may also hold the sheath in place to prevent the sheath from moving axially along the shaft. Exemplary embodiments of sheaths that may be used in conjunction with surgical instrument embodiments of the present disclosure can be found in U.S. application Ser. No. 12/832,580, filed on Jul. 8, 2010 (for "SHEATHS FOR JOINTED INSTRUMENTS") and published as U.S. Pub. No. US 2012/0010628 on Jan. 1, 2012, and in U.S. application Ser. No. 13/739,583, filed Jan. 11, 2013 (for "SHEATH FOR SURGICAL INSTRUMENT") and published as U.S. Pub. No. US 2013/0123805 on May 16, 2013, each of which is hereby incorporated by reference in their entireties.

According to an exemplary embodiment, a seal 202 may be provided within shaft 200, such as to minimize or prevent material that an instrument including shaft 200 is exposed to during a surgical procedure from moving from distal end 220 of shaft 200 towards a proximal end of shaft 200. Seal 202 may be provided at other locations, such as proximate to protrusion 215, according to an exemplary embodiment. Seal 202 may be configured according to seal 149 of the exemplary embodiment of FIG. 2. For instance, seal 202 may be made of, for example, silicone. Seal 202 may be located a distance from distal end 200, such as proximal to wrist 214 or other bendable portion of shaft 200. Further, if instrument includes a joggle joint 217 (discussed further below), seal 202 may be located proximal to joggle joint 217, as shown in FIG. 4.

As shown in the exemplary embodiment of FIG. 4, holes 212 may be located in a relatively distal portion 216 of shaft 200. The portion 216 with the holes 212 may thus provide an open architecture that can extend to and include a distal end 220 of shaft 200, as shown in the exemplary embodiment of FIG. 4, for example, at which an end effector (not shown) may be supported. The location of an open architecture, such as an open architecture formed by holes 212, in shaft 200 may be selected to facilitate cleaning of the instrument and/or to facilitate visual inspection of interior portions of the instrument shaft. Visual inspection, for example, may be helpful in determining areas of the instrument to focus cleaning during a cleaning procedure and/or determining the cleanliness of the instrument after a cleaning procedure. According to an exemplary embodiment, the location of an open architecture may be provided at least at a distal portion 216 of shaft 200 because it is the distal end 220 that is inserted into a patient during a surgical procedure. As a result, the distal end 220 and/or portions of shaft 200 proximate to distal end 220 are more likely to be exposed to materials, such as biomaterials, that may be removed during a cleaning procedure. According to an exemplary embodiment, the portion 216 of shaft having an open architecture may correspond to a length of shaft 200 from distal end 220 that is inserted into a patient during a surgical procedure. However, other lengths, such as a greater length than the insertion distance or a length less than the insertion distance, may be utilized, such as when a sheath is used, insufflation is not performed, or maintaining insufflation pressure is not a concern. Although distal portion 216 having an open architecture may extend proximal to seal 202, as shown in the exemplary embodiment of FIG. 4, distal portion 216 having an open architecture may be located distal to seal 202 (i.e., distal portion 216 having an open architecture may terminate at a location distal to seal 202, which may be proximate to seal 202, or may terminate at seal 202) so that distal portion 216 having an open architecture does not extend distally past seal 202, according to an exemplary embodiment.

According to an exemplary embodiment, the location of an open architecture along the instrument shaft may be located adjacent to joints because moving parts of joints may provide locations where materials to be removed during a cleaning procedure are likely to be located or material may infiltrate into regions of the instrument shaft adjacent to the joints. Joints may include various types of joints with different configurations. For instance, portion 216 of shaft 200 having an open architecture may, for example, include a wrist 214 configured to provide one or more degrees of freedom of movement, such as pitch and/or yaw. Portion 216 may also include a joint 217 proximal to wrist 214 to permit bending of the instrument shaft in various degrees of freedom (e.g., pitch and yaw). Joint 217 may be referred to as a "joggle joint." Joggle joints of the exemplary embodiments described herein may be configured according to the exemplary embodiments of U.S. Pat. No. 7,942,868, published May 17, 2011; U.S. application Ser. No. 11/762,165, filed Jun. 13, 2007 (published as U.S. Pub. No. US 2008/0065105 on Mar. 13, 2008); and U.S. application Ser. No. 12/645,391, filed Dec. 22, 2009 (published as U.S. Pub. No. 2011/0152879 on Jun. 23, 2011).

According to an exemplary embodiment, portion 216 having an open architecture may extend approximately one quarter of the length of shaft 200 from distal end 220. However, other configurations for an open architecture may be used for different instruments that may pose different cleaning challenges. For instance, portion 216 having an open architecture may extend approximately one third of the length of shaft 200 from distal end 220. According to another exemplary embodiment, portion 216 having an open architecture may extend approximately one half of the length of shaft 200 from distal end 220. According to another exemplary embodiment, portion 216 having an open architecture may extend approximately two-thirds of the length of shaft 200 from distal end 220. According to another exemplary embodiment, portion 216 having an open architecture may extend approximately three-quarters of the length of shaft 200 from distal end 220. According to another exemplary embodiment, portion 216 having an open architecture may extend along the full length of shaft 200.

According to an exemplary embodiment, shaft 200 may include a portion 218 that does not include an open architecture, as shown in FIG. 4. A portion 218 may be selected to not have an open architecture because, for example, portion 218 is less likely to experience being soiled with material to be removed during a cleaning process and/or because portion 218 includes features that tend to not collect debris, such as components having smooth surfaces. Thus, an open architecture, such as holes 212 to enhance cleaning and/or facilitate visual inspection, might not be as beneficial for one portion of shaft 200 as another portion that is more likely to experience being soiled with material to be removed during a cleaning procedure. For instance, portion 218 may be proximal to a portion 216 having an open architecture that extends from the distal end 220 of shaft 200.

According to an exemplary embodiment, an open architecture may affect the stiffness of shaft 200. For instance, although holes 212 may enhance cleaning by permitting fluid to penetrate into an interior of shaft and may facilitate visual inspection, holes 212 may reduce the stiffness of shaft 200. As a result, an open architecture may be selected for shaft portions likely to experience material to be removed via cleaning, such as portion 216 extending from the distal end 220 of shaft 200, but not selected for a portion 218 proximal to portion 216. For instance, a portion 218 lacking an open architecture may have a total area of solid surface lacking holes that is greater than a total area of the holes in portion 218. In another instance, portion 218 may lack a plurality of holes arranged in a pattern along both an axial direction and a radial direction of the shaft of a surgical instrument. A portion 218 may lack an open architecture, for example, to preserve a desired stiffness of shaft 200 and provide support for shaft portions distal to portion 218.

Although a shaft of a surgical instrument may include a portion 218 lacking an open architecture relatively close to a distal end portion 216, such as in the exemplary embodiment of FIG. 4, a shaft may include an open architecture extending along portions of the shaft from the distal end to a location anywhere along the shaft up to the proximal end, for example, where a transmission mechanism is located. Turning to FIG. 6, an exemplary embodiment of a shaft 300 of a surgical instrument is shown that includes a portion 314 having an open architecture extending towards or to a distal end 320 of shaft 300. Shaft 300 may include a seal 302 configured according to seal 202 of the exemplary embodiment of FIG. 4. For instance, seal 302 may be located proximal to a wrist 318 or proximal to a joggle joint 319, although other locations may be used, such as proximate to protrusion 316 in FIG. 7.

As shown in the enlarged view of FIG. 7, an exterior wall 310 of shaft 300 may include a plurality of holes 312. As shown in FIG. 7, the plurality of holes 312 may be arranged so that at least one transverse cross-sectional plane 313 and at least one longitudinal cross-section plane 315 each intersect multiple holes 312. Shaft 300 may also include one or more structures to engage with and/or seal with a sheath, such as a protrusion 316 shown in FIG. 7. Portion 314 having an open architecture may be adjacent to one or more joint structures, such as for example, a wrist 318 and another joggle joint 319 like joint 217 in the exemplary embodiment of FIG. 4. According to an exemplary embodiment, portion 314 having an open architecture may extend along a greater part of the length of the shaft from the distal end 320 toward the proximal end than portion 216 in the exemplary embodiment of FIG. 4. According to an exemplary embodiment, portion 314 having an open architecture may extend a length of shaft 300 from distal end 320 by the same amounts discussed above for the exemplary embodiment of FIG. 4.

According to an exemplary embodiment, shaft 300 may have differing diameters along its length. For example, the shaft 300 may include a transition 330 proximal to where the shaft 300 has a first outer diameter and distal to which the shaft has a second outer diameter that differs from the first diameter. For instance, portion 332 of shaft 300 may have a smaller diameter than portion 314. In one exemplary embodiment, portion 332 may have an outer diameter of, for example, about 5 mm, and portion 314 may have an outer diameter of, for example, about 6 mm. According to an exemplary embodiment, the portion of shaft 300 having a larger diameter may extend from transition 330 to distal end 320. Further, a portion of shaft 300 including an open architecture may extend from transition 330 to distal end 320. In other words, the portion of shaft 300 extending from transition 330 to distal end 320 may include holes 312, according to an exemplary embodiment. The exemplary embodiments described herein, however, are not limited to configurations in which the shaft diameter increases in proximal-to-distal direction and instead may have substantially constant cross-sections or cross-sections that increase in the proximal-to-distal direction.

Figure 8:
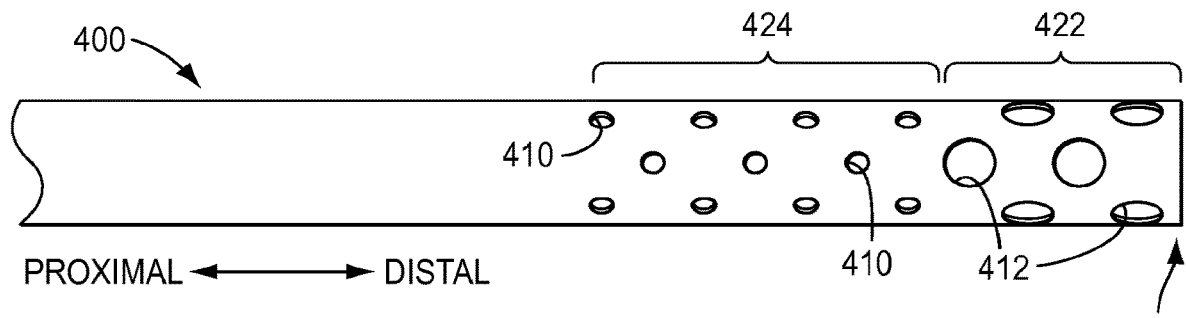
FIG. 8 is a partial side view of an exemplary embodiment of a surgical instrument according to the present disclosure.

As shown in the exemplary embodiments of FIGS. 4-7, holes may have a substantially uniform size along and around the shaft of an instrument. Holes may have a diameter of, for example, about 0.050 inches to about 0.100 inches. In another example, holes may have a diameter of, for example, about 0.060 inches to about 0.080 inches, for example about 0.070 in. However, the embodiments described herein are not limited to holes having a substantially uniform size. Turning to FIG. 8, an exemplary embodiment of a shaft 400 of a surgical instrument is shown that includes holes having differing sizes. As shown in FIG. 8, a first portion 422 at distal end 420 of shaft 400 includes holes 412 having a first size and a second portion 424 proximal to first portion 422 includes holes 410 having a second size that is smaller than holes 412. Holes 412 in first portion 422 may have a larger size, for example, to enhance cleaning and/or facilitate visual inspection because first portion 422 is located at the distal end 420, which is inserted into a patient during a surgical procedure and is more likely to encounter material to be cleaned than, for example, portion 424.

Figure 9:
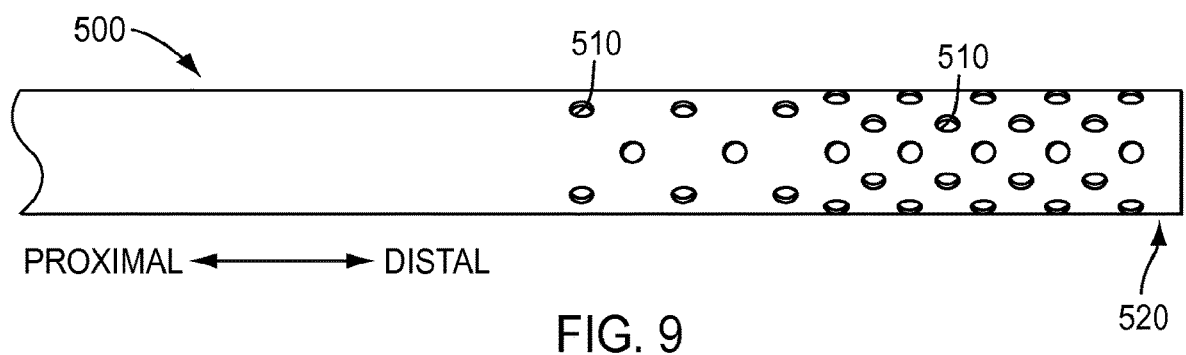
FIG. 9 is a partial side view of yet another exemplary embodiment of a surgical instrument according to the present disclosure.
Figure 10:
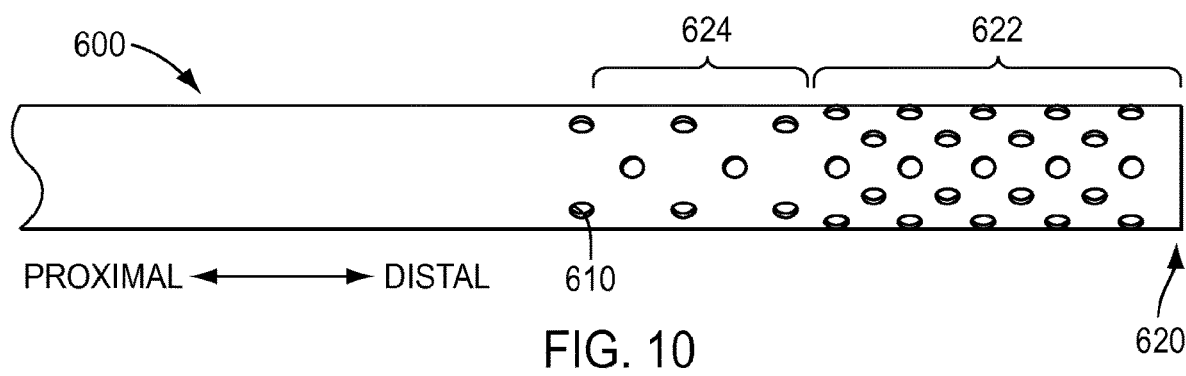
FIG. 10 is a partial side view of another exemplary embodiment of a surgical instrument according to the present disclosure.

Holes in a shaft of a surgical instrument may have a substantially constant density along the shaft, as shown in the exemplary embodiment of FIG. 4. According to an exemplary embodiment, when holes are arranged in rows, as shown in FIG. 5, a spacing of, for example, about 0.10 inches to about 0.30 inches between the centers of holes in adjacent rows may be used. However, the embodiments described herein are not limited to holes having a substantially constant density along the shaft. Turning to FIG. 9, an exemplary embodiment of a shaft 500 of a surgical instrument is shown that includes holes 510 having a density that increases along the shaft toward a distal end 520 of shaft 500. According to an exemplary embodiment, hole density may be increased proximate to distal end 520 of shaft 500 because of an increased likelihood of material soiling the distal end 520 and portions proximate the distal end 520. The density of holes 510 may increase along and/or around the length of shaft 500, as shown in FIG. 9. For instance, the density of holes 510 may vary at a substantially linear rate over a length of shaft 500 or the density may vary at a non-linear rate over the length of shaft 500. In another instance, the density of holes may vary from one region of a shaft to another. As shown in the exemplary embodiment of FIG. 10, a shaft 600 may include a first region 624 having a first hole density and a second region 622 having a second hole density proximate to a distal end 620 of shaft 600, with the second density being greater than the first density or vice versa. Further, although two hole density regions 622, 624 are shown in the exemplary embodiment of FIG. 10, a shaft may include more density regions, such as three, four, five, or more density regions. In addition, the hole density of regions may increase from one region to the next, as depicted in the exemplary embodiment of FIG. 10, or the density may vary differently, such as by increasing from one region to another and then decreasing, along the proximal-distal direction shown in the exemplary embodiment of FIG. 10.

Other features of an open architecture for a shaft of a surgical instrument may be varied. For instance, the hole patterns may be varied from what is shown in the exemplary embodiments of FIGS. 4-10. In another instance, although the shape of holes may be substantially circular, as shown in the exemplary embodiments of FIGS. 4-10, holes may have a different shape, such as an oval, polygons, polygons with rounded corners, or various other shapes as would be readily understood by one of ordinary skill in the art. In another instance, holes may be slots having the shapes described above or other shapes, such as a rectangular or square shape. In another instance, holes may be in the shape of a company logo or in the shape of letters or numbers, which may be used to spell a company name or instrument name or used to list a part number. Holes may be formed in a shaft of a surgical instrument via cutting the shaft with a laser, according to an exemplary embodiment.

The holes of a shaft portion having an open architecture may be arranged in a pattern, as shown in the exemplary embodiments of FIGS. 4-10. Such a pattern may include holes arranged in rows, with the holes of adjacent rows offset from one another in a direction that is substantially perpendicular to the proximal-distal direction, as shown in FIGS. 4-10. Such a pattern of offset rows may, for example, facilitate inspection and stiffness of a shaft. However, the holes in a shaft portion having an open architecture are not limited to this pattern and other patterns may be used.

The hole patterns depicted in various exemplary embodiments also provide an aesthetically pleasing appearance to the instrument, which itself provides a desirable visually distinct aspect of the instrument. Various hole patterns as noted above, therefore, may be chosen solely for aesthetics and to provide a unique and distinctive visual characteristic to the instruments.

As noted above, various surgical instrument embodiments described herein may be used with a sheath. A sheath may be used, for example, to cover holes in at least a portion of the shaft of a surgical instrument, such as to assist with minimizing the introduction of material to the portion of the instrument protected by the sheath. A sheath may be configured according to the embodiments described in U.S. application Ser. No. 12/832,580, filed on Jul. 8, 2010 (for "SHEATHS FOR JOINTED INSTRUMENTS") and published as U.S. Pub. No. US 2012/0010628 on Jan. 1, 2012, and according to the embodiments described in U.S. application Ser. No. 13/739,583, filed on Jan. 11, 2013 (for "SHEATH FOR SURGICAL INSTRUMENT") and published as U.S. Pub. No. US 2013/0123805 on May 16, 2013, each of which is hereby incorporated by reference in their entireties.

Figure 28:
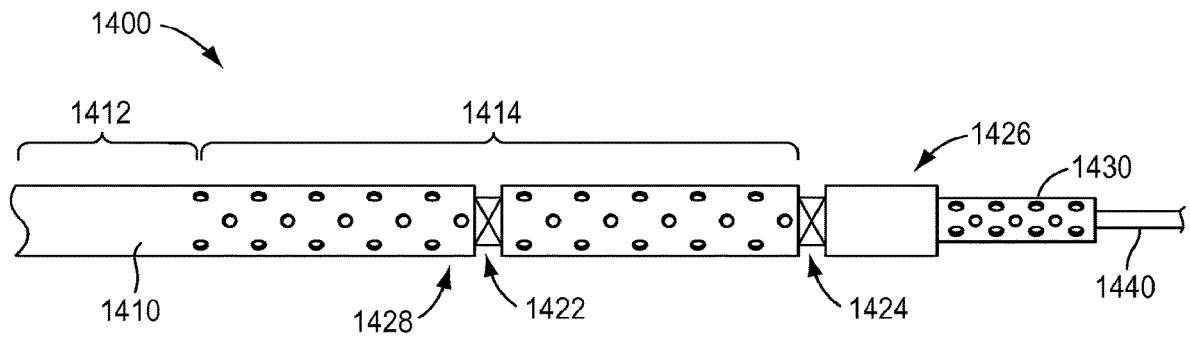
FIG. 28 is a partial side view of an exemplary embodiment of a surgical instrument including a shroud according to the present disclosure.

Although an open architecture for an instrument may include a single layer of open architecture, such as by providing holes through the wall of a shaft of an instrument (such as in the exemplary embodiments of FIGS. 4-7), the open architecture for an instrument may include more than one layer of open architecture. For instance, an instrument may include multiple layers of open architecture. Turning to FIG. 28, an exemplary embodiment of a distal portion 1400 of an instrument is shown. Distal portion 1400 may include a distal portion of an instrument shaft 1410, a seal 1428, a joggle joint 1422, a wrist 1424, and a distal end 1426, as discussed above with regard to the exemplary embodiments of FIGS. 4 and 6. Shaft portion 1410 may include a portion 1412 that does not include an open architecture and a portion 1414 including an open architecture, as discussed above with regard to the exemplary embodiments of FIGS. 4-7. The open architecture may be configured according to the exemplary embodiments of FIGS. 4-10.

Figure 29:
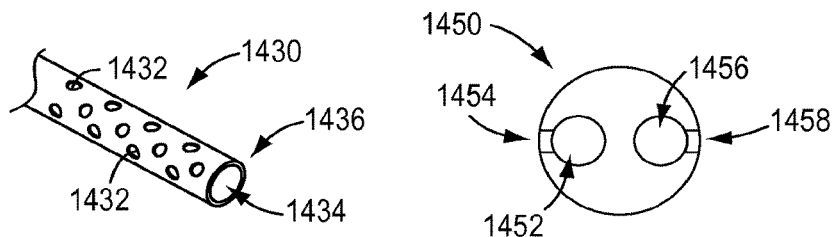
FIG. 29 is a partial perspective view of the shroud of FIG. 28 without an actuation member.
Figure 30:
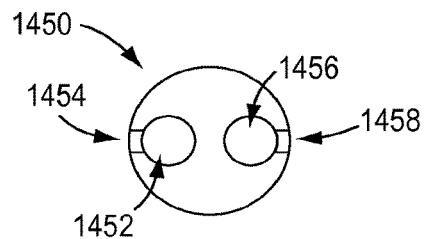
FIG. 30 is a cross-sectional end view of an exemplary embodiment of a shroud.
Figure 31:
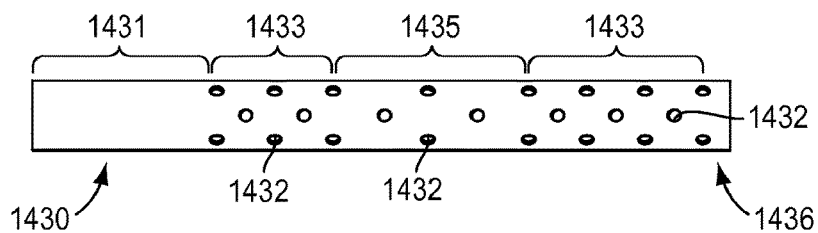
FIG. 31 is a partial side view of an exemplary embodiment of a shroud.

The instrument may further include a shroud 1430 extending through an interior of shaft portion 1410. In the exemplary embodiment of FIG. 28 shroud 1430 extends beyond distal end 1426 of shaft portion 1410 to reveal details of shroud 1430. However, shroud 1430 is not limited to extending beyond distal end 1426 of shaft portion 1410 but instead a distal end of shroud 1430 may be located within the instrument during use of the instrument. For instance, a distal end of shroud 1430 may be located at a distal end of wrist 1424 or located within distal end 1426. According to an exemplary embodiment, one or more actuation member(s) 1440 may extend through shroud 1430. Although a single actuation member 1440 is shown in the exemplary embodiment of FIG. 28, more than one actuation member may extend through shroud 1430. An actuation member 1440 may be, for example, a push/pull actuation member or a pull/pull actuation member to actuate an end effector (not shown) or other component of instrument (push/pull and pull/pull actuation members are described in U.S. Pat. No. 8,545,515, issued on Oct. 1, 2013, which is hereby incorporated by reference in its entirety). For instance, FIG. 29 shows a perspective view of a distal portion of shroud 1430 of FIG. 28, which includes a single lumen 1434 that opens at a distal end 1436 of shroud 1430. Thus, shroud 1430 may be a hollow tube, according to an exemplary embodiment. A single actuation element 1440 (not shown in FIG. 29) may extend through lumen 1434. However, a shroud is not limited to the exemplary embodiment of FIGS. 28 and 29 and may instead have a plurality of actuation members extending through shroud. For instance, the exemplary embodiment of FIG. 30 shows a cross sectional view of a shroud 1450 that includes a first lumen 1452 and a second lumen 1456 that actuation members may extend through. However, other numbers of lumens may be provided in a shroud, such as three lumens, four lumens, five lumens, six lumens or more. Further, other components than actuation members may extend through a lumen of a shroud, such as, for example, a flux conduit, stiffening member, or other instrument components.

A shroud may be provided, according to an exemplary embodiment, as an anti-buckling component by supporting at least a portion of a length of one or more component(s) extending through the shroud, such as actuation member(s), thus increasing the buckling strength of the component(s). However, because component(s) may move relative to a shroud, such as actuation members(s) when they are actuated, it may be possible for material to be introduced between a shroud and a component, such as into a lumen of a shroud through which the component extends. In view of this, it may be desirable to provide at least a portion of a shroud with an open architecture to facilitate cleaning of a shroud, according to an exemplary embodiment. For instance, shroud 1430 may include an open architecture by providing a plurality of holes 1432 in shroud 1430, as shown in the exemplary embodiment of FIG. 29. Holes 1432 may fluidically communicate an environment exterior to shroud 1430 with the internal lumen 1434 of shroud 1430. According to an exemplary embodiment, shroud 1430 may include a portion 1431 that does not include an open architecture and portions 1433 and 1435 that include an open architecture, similar to shaft the open architecture discussed in regard to the exemplary embodiments of FIGS. 4-10. For instance, portions 1433 having an open architecture may have a higher density of holes 1432 than open architecture portion 1435, similar to the exemplary embodiment of FIGS. 9 and 10. Other features of an open architecture of a shroud may be varied, such as, for example, a size of holes, a pattern of holes, and other features discussed above with regard to an open architecture of a shaft, such as in the exemplary embodiments of FIGS. 4-10.

According to an exemplary embodiment, when a shroud includes a plurality of lumens, the holes of an open architecture may communicate with different lumens. For instance, as shown in the exemplary embodiment of FIG. 30, one or more holes 1454 may fluidically communicate with first lumen 1452 while one or more holes 1458 may fluidically communicate with second lumen 1456. According to an exemplary embodiment, when a shroud includes a plurality of lumens, at least one of the lumens may fluidically communicate with one or more holes and at least one of the lumens may not fluidically communicate with a hole. For instance, if a component does not substantially move relative to the shroud (which may create a wicking action that causes material to infiltrate a lumen of the shroud through which the component extends) or material does not otherwise infiltrate a lumen of the shroud through which the component extends, it may not be provide holes that fluidically communicate with the lumen for that particular component.

Because at least a portion of a shroud 1430 may have an open architecture and extend through an interior of a shaft 1410, which itself may have at least a portion having an open architecture, an instrument may have layers of open architecture. However, layers of open architecture may be provided by other components, such as other components that extend through a shaft, including shrouds for flux conduits, stiffening members, and other instrument components.

Figure 11:
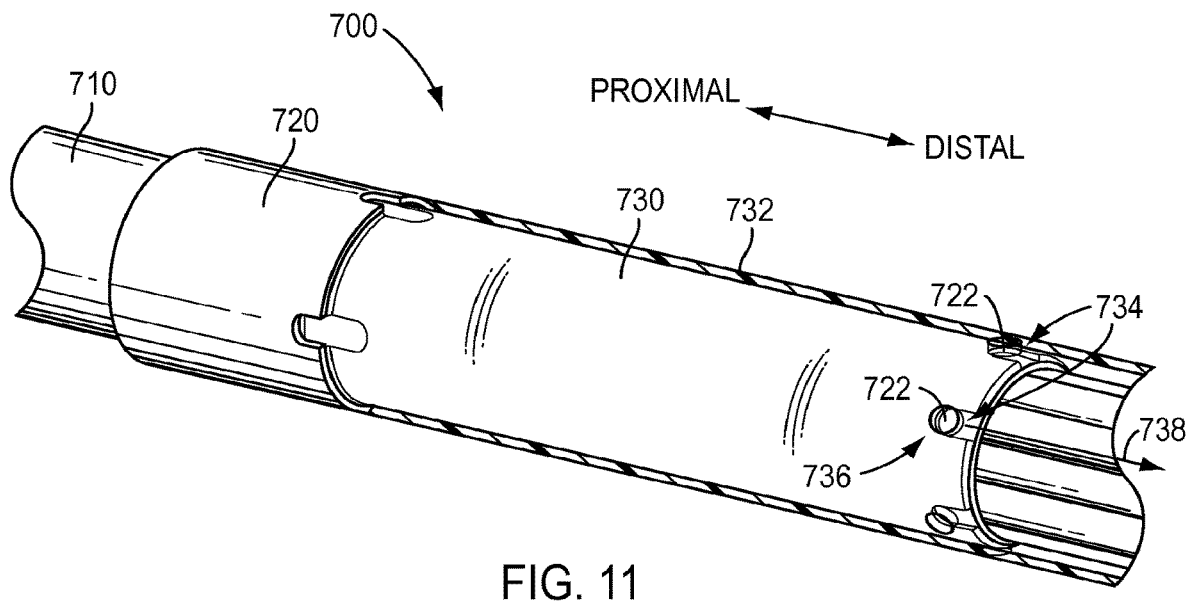
FIG. 11 is a perspective partial cut away view of an exemplary embodiment of a surgical instrument in accordance with the present disclosure.
Figure 12:
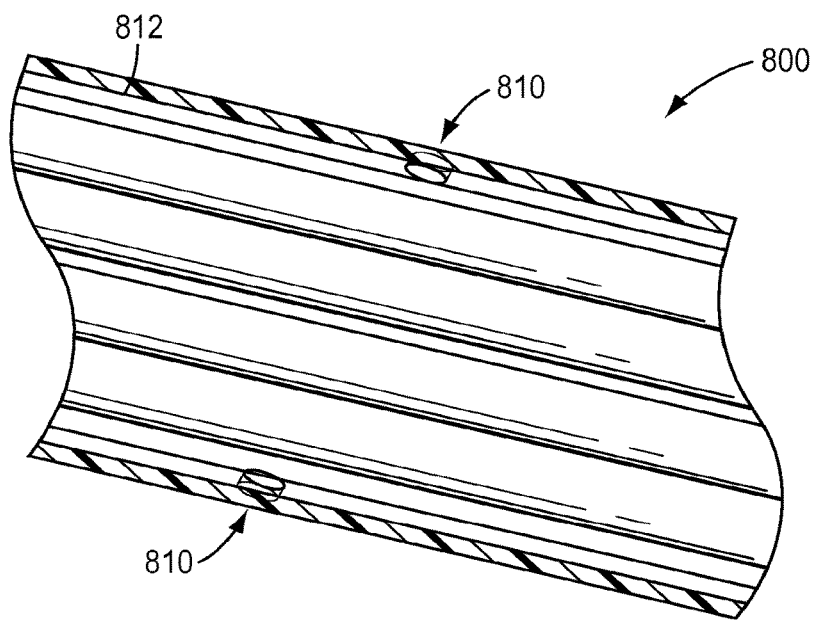
FIG. 12 is a partial cross-sectional view of an exemplary embodiment of a surgical instrument including holes in a sidewall of the shaft of the instrument.

As described above in regard to the exemplary embodiment of FIGS. 4 and 6, a shaft of a surgical instrument may have more than one outer diameter and may include a transition between the different outer diameters. FIG. 11 depicts an exemplary embodiment of a shaft 700 of a surgical instrument that includes a first portion 710 having a first outer diameter and a second portion 720 having a second outer diameter. As shown in the exemplary embodiment of FIG. 11, the first outer diameter may be less than the second outer diameter. A transition may be provided where first portion 710 and second portion 720 meet, which may include a cylindrical member 730. Due to the change in outer diameter between first portion 710 and second portion 720, fluid being flushed through an interior of shaft 700, such as during a cleaning procedure, may experience a change in the inner diameter, which may in turn result in a diminished fluid velocity within the second portion 720 of shaft 700. To address this, features may be provided in shaft 700. For instance, one or more holes 722 may be provided in an exterior wall 732 of shaft 700 at second portion 720 to permit fluid to enter an interior of shaft 700 and mix with fluid being flushed through the interior of shaft 700 and increase the amount of fluid flowing through shaft 700. According to an exemplary embodiment, shaft 700 may include one or more structures to direct the flow of fluid entering holes 722. As shown in the exemplary embodiment of FIG. 11, cylindrical member 730 may include one or more slots 734 fluidically coupled to holes 722 to direct the flow of fluid entering holes 722, such as in a radial direction 736, along shaft 700, such as along an axial direction 735. For instance, cylindrical member 730 may include a slot 734 for each hole 722 in exterior wall 732. According to an exemplary embodiment, a slot 734 may be fluidically connected to a hole 722, have a closed proximal end, and have an open distal end to direct fluid entering the hole 722 along shaft 700, such as in a distal direction. While not wishing to be bound to any particular theory, Applicants submit that the action of directly flowing fluid along the shaft toward a distal end of shaft may assist to draw fluid located proximal to holes 722, causing the fluid to flow along the shaft 700 in the proximal-to-distal direction.

A shaft of a surgical instrument may include one or more structures to influence the flow of fluid in locations other than a transition between different shaft diameters. As shown in the exemplary embodiment of FIG. 12, a shaft 800 may include one or more apertures 810 in an external wall 812 of shaft 800. Apertures 810 may permit fluid external to shaft 800 to pass through external wall 812 and into an interior of shaft 800. As a result, apertures 810 may increase fluid flow and/or turbulence within an interior of shaft 800 by introducing additional fluid into the interior of shaft 800, thus facilitating cleaning of an instrument. According to an exemplary embodiment, apertures 810 are located outside of shaft portions having an open architecture. For instance, apertures 810 may be located proximal to the shaft portions having an open architecture. According to an exemplary embodiment, apertures 810 may have a diameter of, for example, about 0.030 inches to about 0.040 inches, for example about 0.035 inches.

As discussed above, fluid may be forced through an interior of a shaft of an instrument during a cleaning procedure. In various exemplary embodiments herein, fluid may be introduced to flow directly into an interior along a substantially axial path of the shaft and/or may be introduced into the interior of the shaft from outside the exterior surface of the shaft, such as in a direction substantially transverse to a longitudinal axis of shaft. A surgical instrument may in various exemplary embodiments include one or more structures to facilitate flushing of fluid through an interior of the shaft.

The discussion of the exemplary embodiments of FIGS. 3-12 regard surgical instruments for a robotic surgical system, which may include, for example, a variety of therapeutic instruments, such as, forceps or graspers, needle drivers, scalpels, scissors, cauterizing tools, staplers, and other surgical instruments recognized by one of ordinary skill in the art. However, as discussed above, the features of the exemplary embodiments described herein also can be applied to an endoscopic camera or other sensor instrument used with a robotic surgical system.

Figure 13:
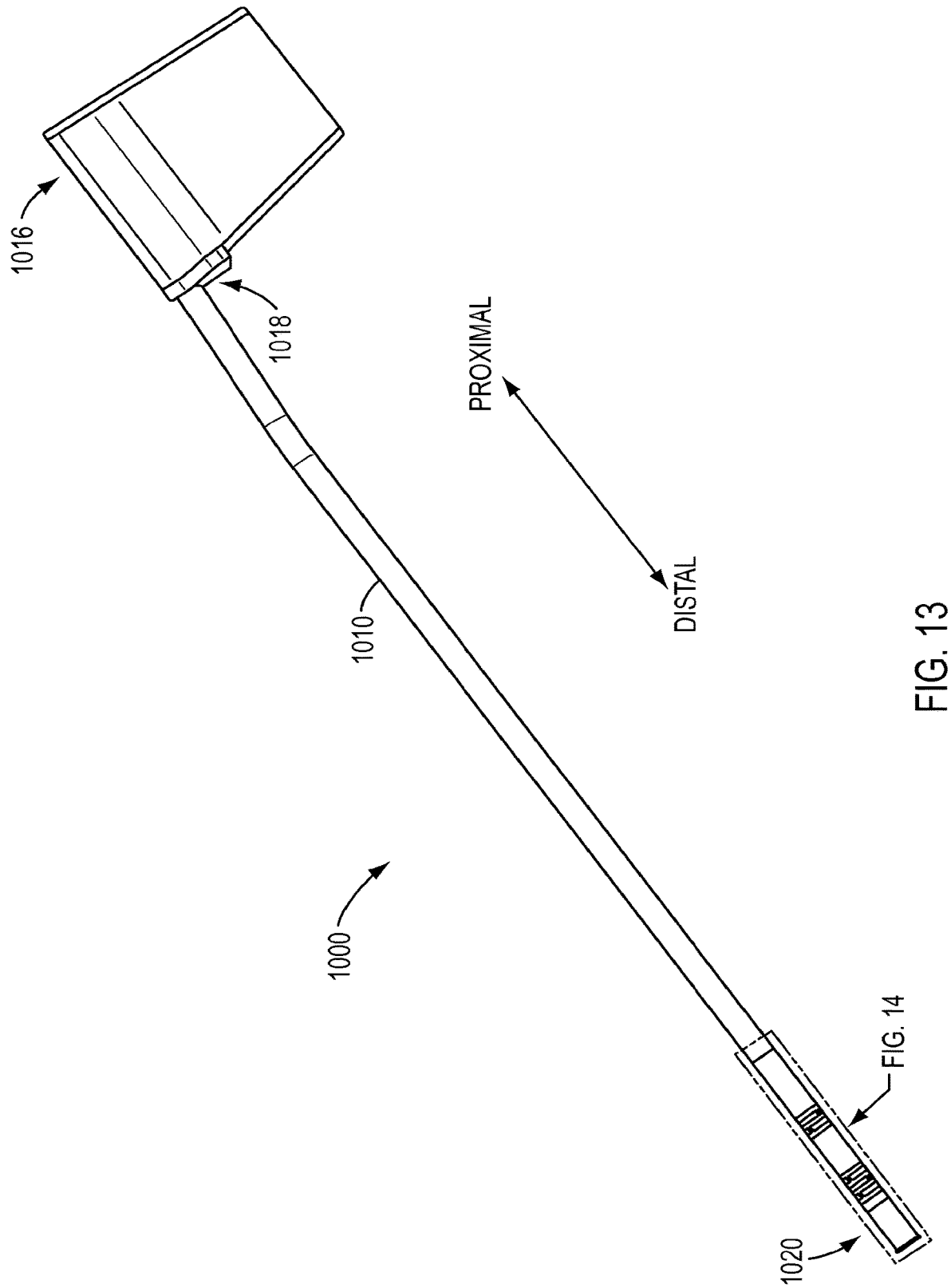
FIG. 13 is a perspective view of an exemplary embodiment of an endoscopic camera instrument in accordance with the present disclosure.

Turning to FIG. 13, an exemplary embodiment of an instrument 1000 is shown that includes a shaft 1010, a distal end 1020, and a proximal housing 1016. Instrument 1000 may be, for example, a surgical instrument with an end effector, an endoscopic camera instrument, or other type of surgical instrument. Therefore, the features of the exemplary embodiments of FIGS. 13-17 are not limited to camera instruments and may be utilized in a surgical instrument having an end effector, such as the instrument of the exemplary embodiment of FIG. 2.

Figure 14:
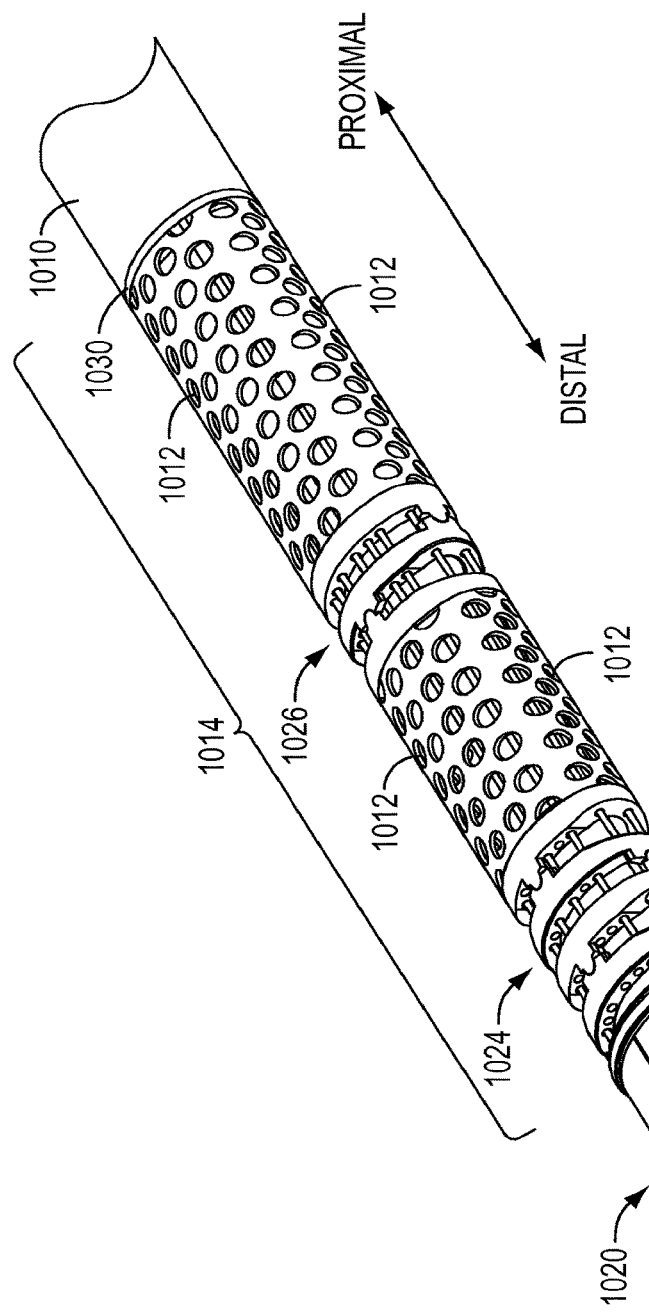
FIG. 14 is the enlarged view labeled FIG. 14 in FIG. 12.

As shown in FIG. 14, which is an enlarged view of the distal portion of instrument 1000, instrument 1000 may be a camera instrument having a distal end 1020 including an aperture 1022 for an optical device (not shown) to view a work site and the operation of surgical instruments within a patient. According to an exemplary embodiment, camera instrument 1000 may be an endoscopic camera configured according to the embodiments described in U.S. application Ser. No. 14/080,384, filed on Nov. 14, 2013 (for "LOW CAPACITANCE ENDOSCOPIC SYSTEM") and published as U.S. Pub. No. US 2014/0155758 A1 on Jun. 5, 2014, and U.S. application Ser. No. 14/080,403, filed on Nov. 14, 2013 (for "ENDOSCOPIC SYSTEM WITH ELECTROMAGNETIC INTERFERENCE SHIELDING") and published as U.S. Pub. No. US 2014/0135579 A1 on May 15, 2014, each of which are hereby incorporated by reference in their entireties. Housing 1016 may include a port 1018 that is in flow communication with a manifold (not shown) so as to receive a fluid to be flushed through an interior of shaft 1010, as described in the exemplary embodiment of FIG. 3.

Instrument 1000 may further be fitted with a sheath (not shown) to cover at least portion of the shaft of the instrument 1000. For example, a sheath may be connected to a portion 1023 at distal end 1020, such as via shrink fitting, and extend along shaft 1010 in a distal-to-proximal direction. A sheath for an instrument 1000 may comprise, for example, expanded polytetrafluoroethylene (ePTFE). Shaft 1010 may include one or more protrusions, as described in the exemplary embodiments of FIGS. 4 and 6, to contact and/or seal against an interior surface of a sheath. For instance, portion 1023 may include at least one protrusion, which may abut against a sheath to minimize or eliminate sliding of the sheath off of distal end 1020 of instrument 1000. According to an exemplary embodiment, the protrusion may be a single circumferential protrusion or may be a plurality of discrete protrusions, such as a pair of protrusions on opposite sides of distal end 1020. However, instrument 1000 need not include a protrusion to seal with a sheath, such as when the sheath is connected at portion 1023. A sheath for an instrument 1000 may be configured according to the exemplary embodiments described in U.S. application Ser. No. 12/832,580, filed on Jul. 8, 2010 and published as U.S. Pub. No. US 2012/0010628 on Jan. 1, 2012, and in U.S. application Ser. No. 13/739,583, filed Jan. 11, 2013 and published as U.S. Pub. No. US 2013/0123805 on May 16, 2013.

Instrument 1000 may further include one or more joints. Joints may be of different types having different configurations. For instance, instrument 1000 may include a wrist 1024 providing one or more degrees of freedom of movement, such as pitch and/or yaw, and a joggle joint 1026 proximal to wrist 1024 to permit bending of camera instrument 1000. However, an instrument 1000 is not limited to this configuration and may include various combinations of joints, such as wrists and/or joggle joints. Because distal end 1020 of instrument 1000 may be inserted into the body of a patient during a surgical procedure and because instrument 1000 may include one or more joints, which may include moving parts, instrument 1000 may have an open architecture along at least part of the nonjointed parts of the shaft. For example, shaft 1010 may include holes 1012, as shown in the exemplary embodiment of FIG. 14. Holes 1012 may be configured according to the exemplary embodiments of FIGS. 4-10 to enhance cleaning and visual inspection of camera instrument 1000. For instance, when instrument 1000 is a camera instrument, only a portion of shaft 1010 may include an open architecture due to the relatively limited amount of exposure of camera instrument 1000 to material to be cleaned. According to an exemplary embodiment, instrument 1000 may include a distal portion 1014 proximate to distal end 1020 that includes holes 1012, with the remainder of shaft 1010 proximal to portion 1014 having a substantially continuous solid outer surface (e.g., free of holes 1012). The portion 1014 of shaft 1010 including holes 1012 be adjacent to joints, as shown in the exemplary embodiment of FIG. 11.

Instrument 1000 may include one or more actuation members 1038 (e.g., cables) to actuate components (see FIG. 15), such as joints, as well as flux transmission conduits (not shown). Flux transmission conduits may be conduits to provide energy to an end effector, such as in the case of instrument 1000 being a surgical instrument with an end effector, or the conduits may supply other types of fluxes, such as fluid, suction, collected light to provide optical data and/or light to illuminate a work site and other components in the case that instrument 1000 is a camera instrument. Thus, the features of the exemplary embodiment of FIG. 15 may be used in a camera instrument or a surgical instrument including an end effector.

Figure 15:
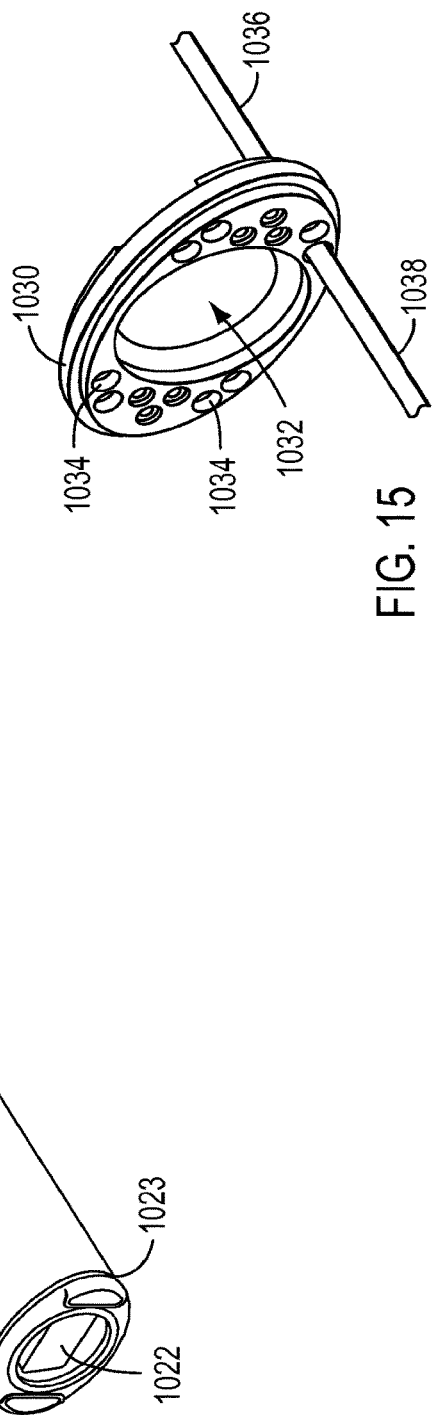
FIG. 15 is a perspective view of an exemplary embodiment of a seal for a camera device in accordance with the present disclosure.

According to an exemplary embodiment, instrument 1000 may include a seal 1030 located inside shaft 1010 to seal against components extending along shaft 1010 and to seal against an interior surface of shaft 1010 so that portion 1014 with open architecture is segregated from a remainder of shaft 1010 proximal to seal 1030. According to an exemplary embodiment, when instrument 1000 is a surgical instrument with an end effector, seal 1030 may correspond to seal 149 of the exemplary embodiment of FIG. 2. Seal 1030 may include, for instance, a central aperture 1032, as shown in FIG. 15, for one or more flux transmission conduits, such as energy conduits or conduits to provide optical data and/or illuminate a work site. Central aperture 1032 may be sized and otherwise configured to seal against the one or more flux transmission conduits, according to an exemplary embodiment. Further, seal 1030 may include one or more apertures 1034 for actuation members 1038, such as cables to actuate joints.

According to an exemplary embodiment, central aperture 1032 and apertures 1034 may include sealing structures, such as a compliant material that presses against structures passing central aperture 1032 and apertures 1034. Further, apertures 1034 may be sized and otherwise configured to seal against actuation members 1038, according to an exemplary embodiment. Actuation members 1038 may include structures to provide a degree of protection to the actuation members 1038 proximal to seal 1030, such as from wear and other forms of damage from physical contact. As shown in the exemplary embodiment of FIG. 15, the actuation members 1038 may be covered with tubes 1036 proximal to seal 1030. Further, tubes 1036 may extend through seal 1030 to a location distal to seal 1030 so that tubes 1036 may be sealed with seal 1030. Thus, seal 1030 may advantageously minimize or prevent the flow of material along actuation members 1038 (such as due to a wicking or capillary action) in a distal to proximal direction in the exemplary embodiment of FIG. 15, effectively sealing off a distal end 1020 of instrument 1000 from a portion proximal to seal 1030. However, tubes 1036 may have other configurations and may instead end at seal 1030 instead of extending distally past seal 1030 in the exemplary embodiment of FIG. 15. Tubes 1036 may comprise, for example, metal, such as, for example, stainless steel. In another example, tubes 1036 may comprise a composite material, such as, for example, a composite polymer material.

When instrument 1000 includes an open architecture, it may be desirable to provide protection to the components within instrument 1000 from wear and other forms of damage from physical contact. For instance, optical data/illumination conduits and other camera components (such as when instrument 1000 is a camera instrument) and/or other flux transmission conduits (such as, for example, energy conduits for a surgical instrument having an end effector) and/or actuation members (such as an actuation member for an end effector) may pass through joints (when instrument 1000 includes these features) and/or through a portion 1014 of shaft having an open architecture. Because joints and portion 1014 of shaft having an open architecture may permit access to an interior of shaft 1010, it may be desirable to provide protection for such conduits and/or components through such regions of instrument 1000, such as to separate the conduits and other components from articulated portions of joints and minimize pinching and wear of the conduits and other components and/or to act as a barrier to keep components passing through an open architecture substantially dry.

Figure 16:
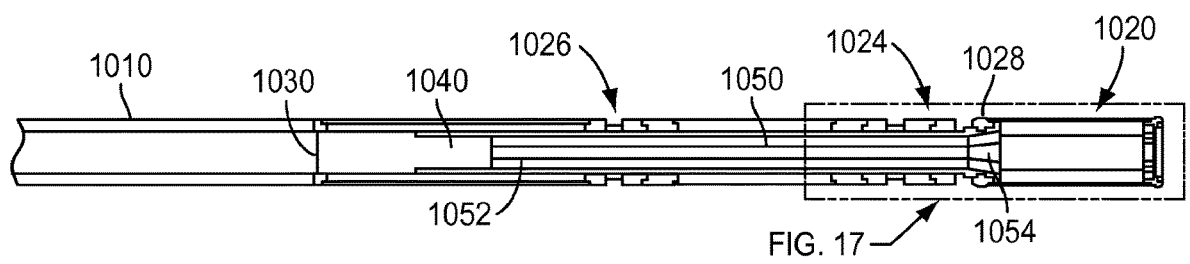
FIG. 16 is a partial side cross-sectional view of an exemplary embodiment of an endoscopic camera instrument according to the present disclosure.
Figure 17:
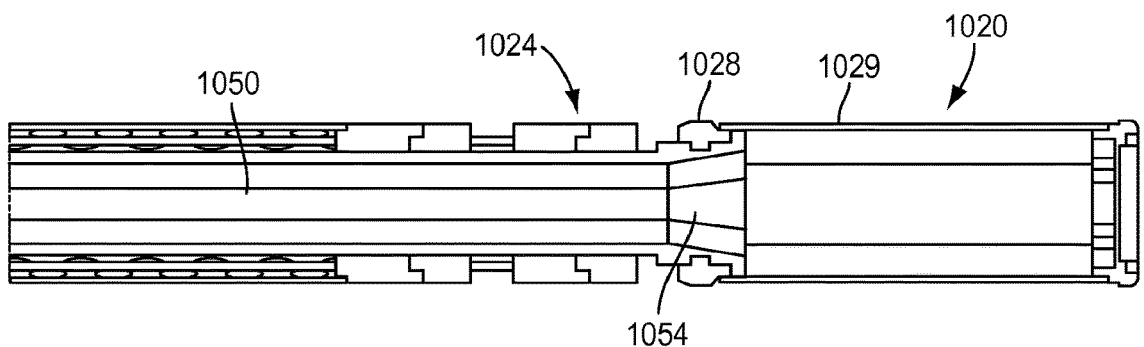
FIG. 17 is the enlarged view labeled FIG. 17 in FIG. 16.

Turning to FIGS. 16 and 17, a cross-sectional view of instrument 1000 is depicted. As noted above, instrument 1000 may be a camera instrument or a surgical instrument with an end effector, such as the instrument of the exemplary embodiment of FIG. 2. As illustrated, instrument 1000 includes a sleeve 1050 inside shaft 1010 that conduits may extend through to distal end 1020 of instrument 1000. Sleeve 1050 may extend through the portion 1014 of shaft 1010 including an open architecture so that conduits, electrical wires, actuation members, and/or other components extending through an interior of sleeve 1050 are not exposed via the open architecture. Furthermore, sleeve 1050 may extend through the region of shaft 1010 including joints, such as wrist 1024 and joggle joint 1026, so that conduits, electrical wires, actuation members, and/or other components extending through sleeve 1050 are provided with protection when instrument 1000 is articulated via wrist 1024 and/or joint 1026. Because sleeve 1050 extends through portions of instrument 1000 that may be articulated, such joints, sleeve 1050 may be flexible. As shown in the exemplary embodiment of FIG. 16, sleeve 1050 may be located distal to seal 1030 so that conduits, electrical wires, and/or other components passing through central aperture 1032 of seal 1030 may enter seal 1030 and extend towards distal end 1020 of instrument 1000. According to an exemplary embodiment, sleeve 1050 may comprise, for example, silicone or other flexible material recognized by one of ordinary skill in the art. Further, sleeve 1050 may be transparent or translucent to permit viewing of conduits and/or other components inside sleeve 1050.

Because sleeve 1050 may pass through a portion of an instrument having an open architecture, sleeve 1050 may be sealed to minimize or prevent material from entering an interior of sleeve 1050. For instance, sleeve 1050 may seal components extending through an interior of sleeve 1050 from surrounding fluids, such as liquids and/or gases. Thus, sleeve 1050 may keep components passing through an interior of sleeve 1050 substantially dry, such as during a surgical procedure and/or during a cleaning procedure. For instance, a proximal end 1052 of sleeve 1050 may be connected to a jacket 1040 extending through an interior of shaft 1010 along a proximal-distal direction. According to an exemplary embodiment, when an instrument includes the seal 1030 of the exemplary embodiment of FIG. 15, seal 1030 may seal against an interior surface of jacket 1040, although seal 1030 may seal against an interior surface of shaft 1010 when jacket 1040 is absent from an instrument. A proximal end 1052 of sleeve 1050, for example, may be sealed to jacket 1040. According to another exemplary embodiment, proximal end 1052 of sleeve 1050 may be sealed to an interior surface of shaft 1010, such as when jacket 1040 is not present, although proximal end 1052 may instead seal to jacket 1040 when jacket 1040 is present in an instrument. Further, a distal end 1054 of sleeve 1050 may be sealed to a distal end 1020 of the instrument, such as a location distal to one or more joints, such wrist 1024 and/or a joggle joint 1026. For instance, distal end 1054 of sleeve 1050 may be sealed to a distal disk 1028 of wrist 1024 and/or to an end piece 1029 of instrument, as shown in FIG. 17. According to an exemplary embodiment, sleeve 1050 may be connected or otherwise sealed to instrument components, such as jacket 1040, shaft 1010, disk 1028, and/or end piece 1029, by, for example, overmolding sleeve 1050 onto the camera device components, adhesively bonding sleeve 1050 to instrument components, and other joining methods recognized by one of ordinary skill in the art.

Cleaning Fluid Distributors

Figure 18:
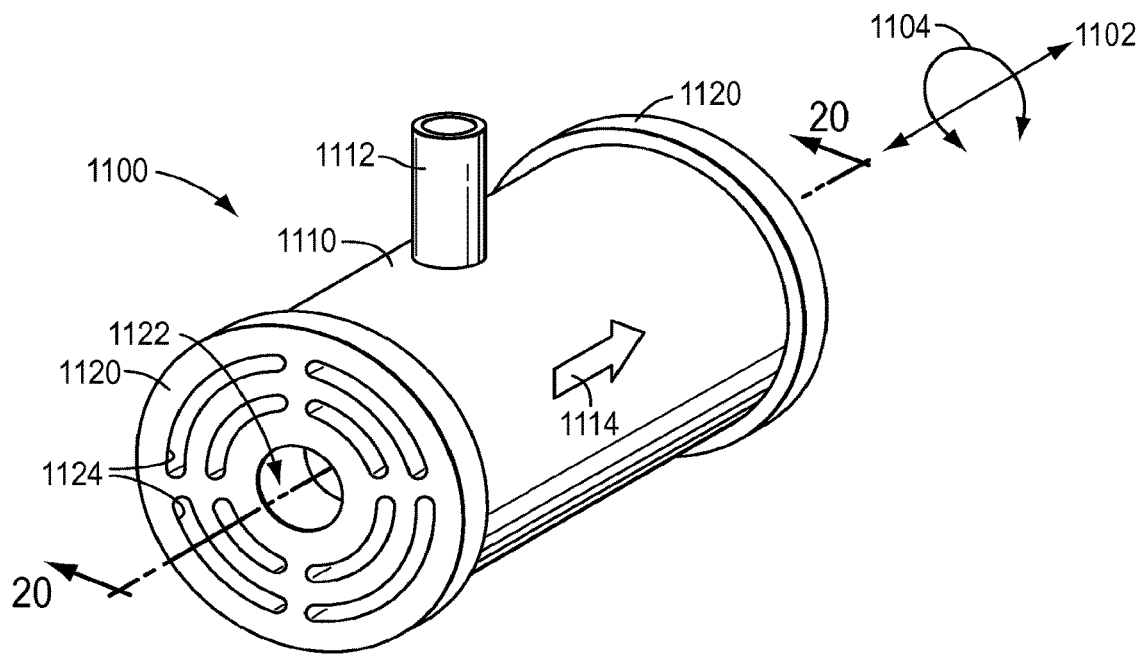
FIG. 18 is a perspective view of an exemplary embodiment of a cleaning device in accordance with the present disclosure.

Aside from including features in surgical and camera instruments to facilitate cleaning, the present disclosure contemplates various cleaning devices separate from surgical or camera instruments that can facilitate cleaning of surgical instruments. Turning to FIG. 18, an exemplary embodiment of a cleaning device in the form of a cleaning fluid distributor 1100 in accordance with the present disclosure is shown. Cleaning fluid distributor 1100 may include a body 1110 and end pieces 1120. As shown in the exemplary embodiment of FIG. 18, body 1110 may include a port 1112 configured to connect to a source providing fluid for a cleaning procedure. Port 1112 may be configured to quickly and easily connect with a fluid source, such as a hose delivering fluid or an automated reprocessing device, such as the exemplary embodiments described in International Application No. PCT/US14/49454, filed on Aug. 1, 2014 (for "DEVICES, SYSTEMS, AND METHODS FOR SURGICAL INSTRUMENT REPROCESSING), which is hereby incorporated by reference in its entirety. According to an exemplary embodiment, port 1112 may include a luer type of fitting, although such a fitting is nonlimiting and exemplary only. For instance, port 1112 may include a fitting that locks to a connection and may only be disconnected by a user actuating a release mechanism, such as the connection described above for the port 190 of the exemplary embodiments of FIGS. 3 and 27. Body 1110 may further include a visual indicator 1114, such as, for example, an arrow, text, or other visual indicator to indicate a direction that a surgical instrument may be inserted through cleaning fluid distributor 1100.

Cleaning fluid distributor 1100 may include end pieces 1120 attached to each axial end of body 1110, as shown in the exemplary embodiment of FIG. 18. However, cleaning fluid distributor 1100 is not limited to including two end pieces 1120. For instance, cleaning fluid distributor 1100 may include, for example, one end piece 1120 at one axial end of body 1110, with the other axial end of body 1110 including the one or more apertures of an end piece 1120, as described below. An end piece 1120 may include a central opening 1122 configured to receive a surgical instrument inserted into cleaning fluid distributor 1100. According to an exemplary embodiment, central opening 1122 may be sized to receive and/or guide a surgical instrument or a camera device during its insertion into the fluid distributor 1100. For instance, central opening 1122 may be sized to guide a surgical instrument into distributor 1100 but also permit relative movement between distributor 1100 and an instrument inserted within distributor 1100, such as along axial direction 1102 and along rotational direction 1104 shown in FIG. 18. Further exemplary embodiments of cleaning devices discussed below may also be configured to permit relative movement along axial direction 1102 and/or rotational direction 1104. According to an exemplary embodiment, central opening 1122 may have a diameter of, for example, that ranges from about 0.250 inches to about 0.750 inches. According to an exemplary embodiment, central opening 1122 may have a diameter of, for example, about 0.250 inches to about 0.300 inches for a surgical instrument having an end effector. According to an exemplary embodiment, central opening 1122 may have a diameter of, for example, about 0.600 inches to about 0.750 inches for a camera instrument. Central openings 1122 may be configured to provide a clearance between the surface forming openings 1122 and an outer surface of a surgical instrument. For example, central openings 1122 may be configured to provide a clearance of about 0.020 inches to about 0.050 inches on each side of a surgical instrument.

Figure 19:
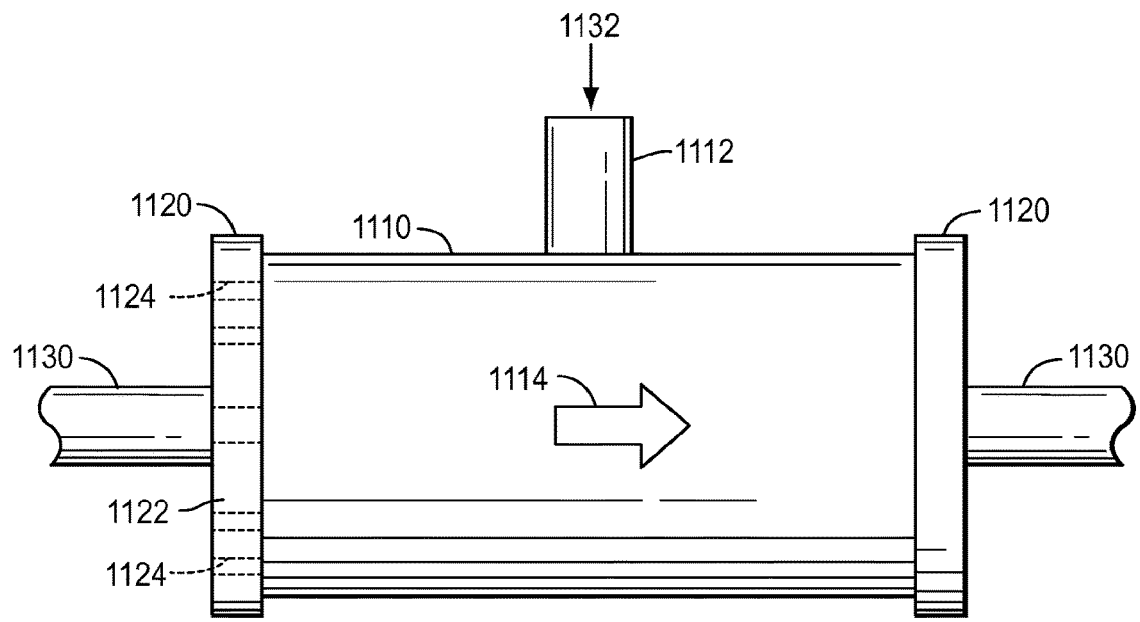
FIG. 19 is a side view of the cleaning device of FIG. 18 depicted with a surgical instrument inserted through the cleaning device.

For instance, a shaft 1130 of a surgical instrument may be inserted through central openings 1122 of the end pieces 1120 so that the shaft 1130 may be inserted through a cleaning fluid distributor 1100, as shown in the exemplary embodiment of FIG. 19. According to an exemplary embodiment, fluid 1132 may be supplied to cleaning fluid distributor 1100 via port 1112 during a cleaning procedure and delivered to an exterior of the surgical instrument located inside of the cleaning fluid distributor 1100, as will be described below. Although cleaning fluid distributor 1100 may be arranged to primarily deliver fluid to an exterior of a surgical instrument, fluid may also penetrate to an interior of the surgical instrument during a cleaning procedure using cleaning fluid distributor 1100, such as at portions of the surgical instrument including an open architecture.

Cleaning fluid distributor 1100 also may include one or more features to remove fluid from cleaning fluid distributor 1100. As shown in the exemplary embodiment of FIG. 18, an end piece 1120 may include one or more openings 1124 that pass through end piece 1120 and are in flow communication with an interior of cleaning fluid distributor 1100. Thus, openings 1124 may permit fluid inside body 1110, including material flushed from an instrument, to exit cleaning fluid distributor 1100 through openings 1124. The number of openings 1124 may be selected based on, for example, a desired amount of turbulence of the fluid flow, a flow rate of the fluid, and other parameters recognized by one of ordinary skill in the art for a fluid used in a cleaning procedure. Openings 1124 may also be used to direct spraying of fluid from inside body 1110 to the exterior of body 1110, such as to minimize spraying of a user, so the number and/or shape of openings 1124 may be selected in view of this consideration as well. For example, an end piece 1120 could include eight openings 1124, although other configurations using fewer or greater numbers of openings 1125 may be used. According to an exemplary embodiment, openings 1124 may have an arcuate shape, as shown in FIG. 18. Further, openings 1124 may be arranged in generally circular configurations, which may be concentric with central opening 1122, as shown in FIG. 18. Openings may be arranged in one or more generally circular configurations, with two being shown in FIG. 18, and a single circular configuration being shown in FIG. 19. However, the shape and arrangement of openings 1124 are not limited to the embodiments described herein and other shapes and arrangements of openings 1124 may be used. Further, a feature to remove fluid from cleaning fluid distributor 1100 may include structures other than openings 1124. For instance, a second port (not shown) similar to port 1112 may be provided to remove fluid from inside cleaning fluid distributor 1100.

Figure 20:
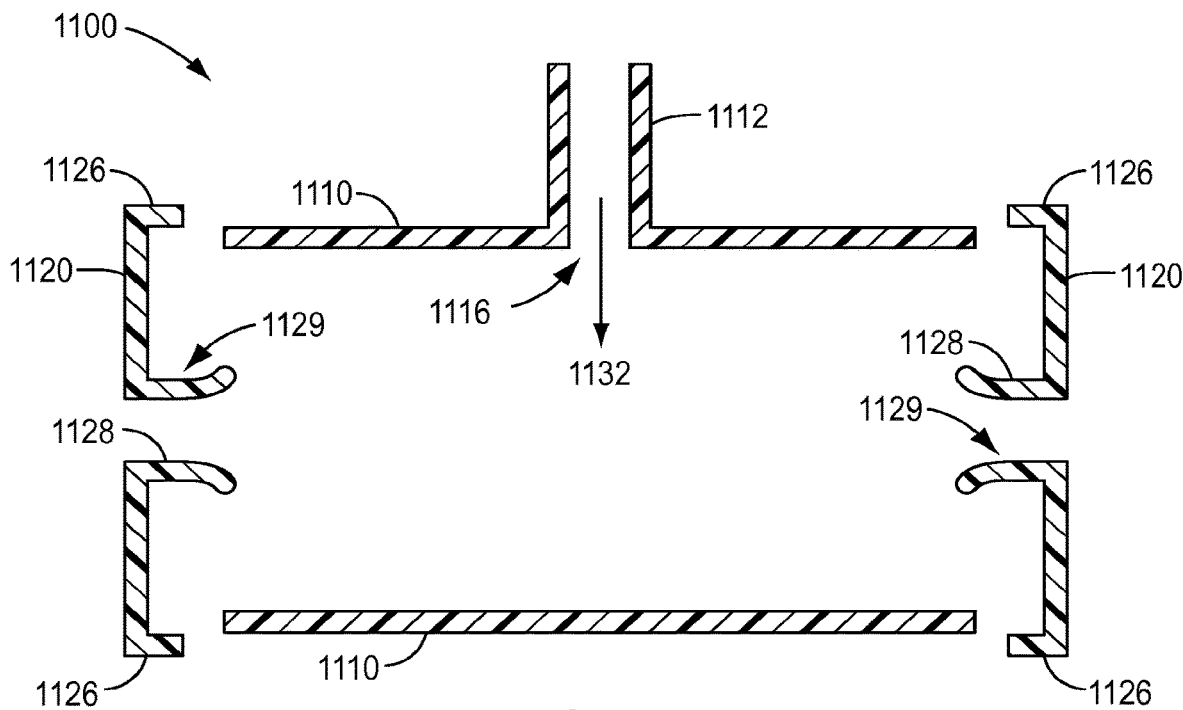
FIG. 20 is a cross-sectional view of the cleaning device of FIG. 18 taken along lines 20-20 in FIG. 18 and with the end pieces shown disengaged from the body of the cleaning device.

As described above, end pieces 1120 may be attached to body 1110 of cleaning fluid distributor 1100. End pieces 1120 may be removed to facilitate maintenance of cleaning fluid distributor 1100, such as to permit removal of excess material remaining within body 1110. For instance, end pieces 1120 may be attached to body 1110 by, for example, screw threads, friction fitting, or other attachment means recognized by one of ordinary skill in the art. Turning to FIG. 20, a cross-sectional view is shown along line 20-20 of FIG. 18, with end pieces 1120 removed from body 1110. Features to attach an end piece 1120 to body 1110 may be provided on, for example, a flange 1126 of end piece 1120. Flange 1126 may be configured, for example, to engage and/or fit over body 1110 to attach end piece 1120 to body 1110. According to an exemplary embodiment, an end piece 1120 may include a passage 1128 to guide and/or align an instrument through cleaning fluid distributor 1100. Passage 1128 may have a generally cylindrical shape. Further, passage 1128 may have a flared end 1129, as shown in the exemplary embodiment of FIG. 20, such as to guide an end of an instrument into passage 1128.

Structures may be provided inside of a cleaning device to direct the flow of a cleaning fluid during a cleaning procedure. As shown in the exemplary embodiment of FIG. 20, a body 1110 of a cleaning fluid distributor 1100 may include a single aperture 1116 to deliver fluid 1132 to an interior of cleaning fluid distributor 1100. According to an exemplary embodiment, aperture 1116 may be directly connected to port 1112, as shown in FIG. 20. Although aperture 1116 may have the inner diameter as port 1112, as shown in the exemplary embodiment of FIG. 20, aperture 1116 may have a smaller diameter, such as to provide a localized increase in fluid velocity. Fluid having an increased fluid velocity may facilitate cleaning by facilitating removal of material from an instrument. A direction of fluid 1132 flowing out of aperture 1116 may be in a radial direction that is substantially perpendicular to a longitudinal axis of an instrument shaft inserted through distributor 1100, although other configurations of aperture 1116 may be used to provide other angles of fluid delivery.

Figure 21:
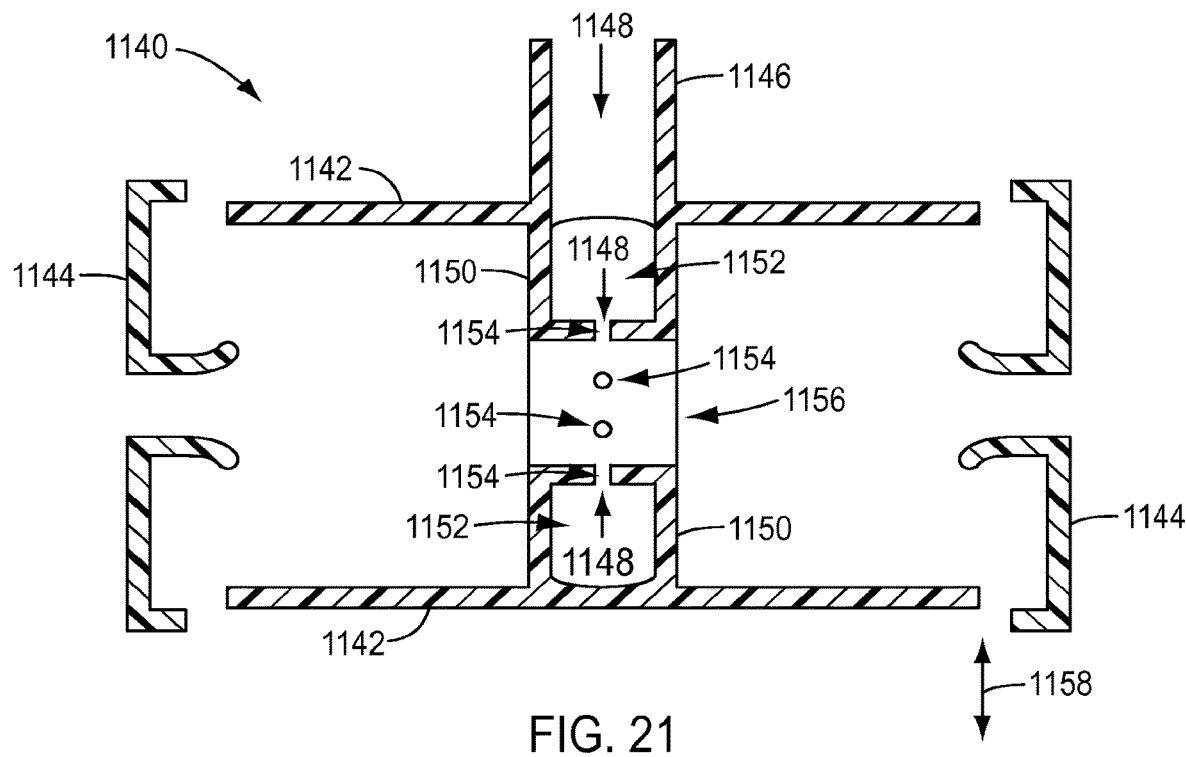
FIG. 21 is a side cross-sectional view of another exemplary embodiment of a cleaning device in accordance with the present disclosure.
Figure 22:
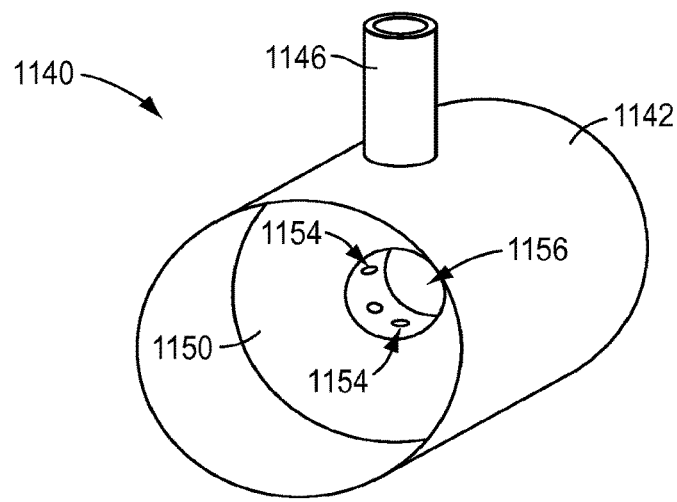
FIG. 22 is a perspective view of the cleaning device of FIG. 21.

According to an exemplary embodiment, a cleaning device may include more than one aperture to direct a fluid into an interior of the cleaning device. Turning to FIG. 21, an exemplary embodiment of a cleaning device 1140 is shown that includes a body 1142, end pieces 1144, and a port 1146 configured to receive fluid 1148. Cleaning device 1140 may further include a manifold 1150 in the interior of body 1142 forming a chamber 1152 that is in flow communication with port 1146. As shown in FIG. 22, which is a perspective view of cleaning device 1140, manifold 1150 may have an annular shape with a central passage 1156 for passage of a surgical instrument, such as when body 1142 has a cylindrical shape, as shown in FIG. 22. However, manifold 1150 is not limited to an annular shape and may instead have other shapes, such as when body 1142 does not have a cylindrical shape.

As shown in FIGS. 21 and 22, manifold 1150 may include one or more holes 1154 fluidically connected to chamber 1152. Thus, fluid 1148 supplied to chamber 1152 from port 1146 may exit chamber 1152 into central passage 1156 via holes 1154, such as to distribute fluid 1148 to a surgical instrument inserted into cleaning device 1140 and through central passage 1156. According to an exemplary embodiment, manifold 1150 may include, for example, one hole 1154, two holes 1154, three holes 1154, four holes 1154, five holes 1154, six holes 1154, seven holes 1154, eight holes 1154, nine holes 1154, ten holes 1154, eleven holes 1154, twelve holes 1154, or more. In various exemplary embodiments, the number and arrangement of holes can be selected based on desirable fluid flow rate and velocity to achieve desired cleaning. According to an exemplary embodiment, a number of holes 1154 may be selected so that rotational movement between distributor 1140 and an instrument inserted within distributor 1140 is not necessary to distribute cleaning fluid over an exterior of the instrument. Further, holes 1154 may have a diameter smaller than an inner diameter of port 1146, as shown in the exemplary embodiment of FIG. 21. This may provide a localized increase in fluid velocity and a spray of fluid over an instrument inserted through central passage 1156.

Figure 23:
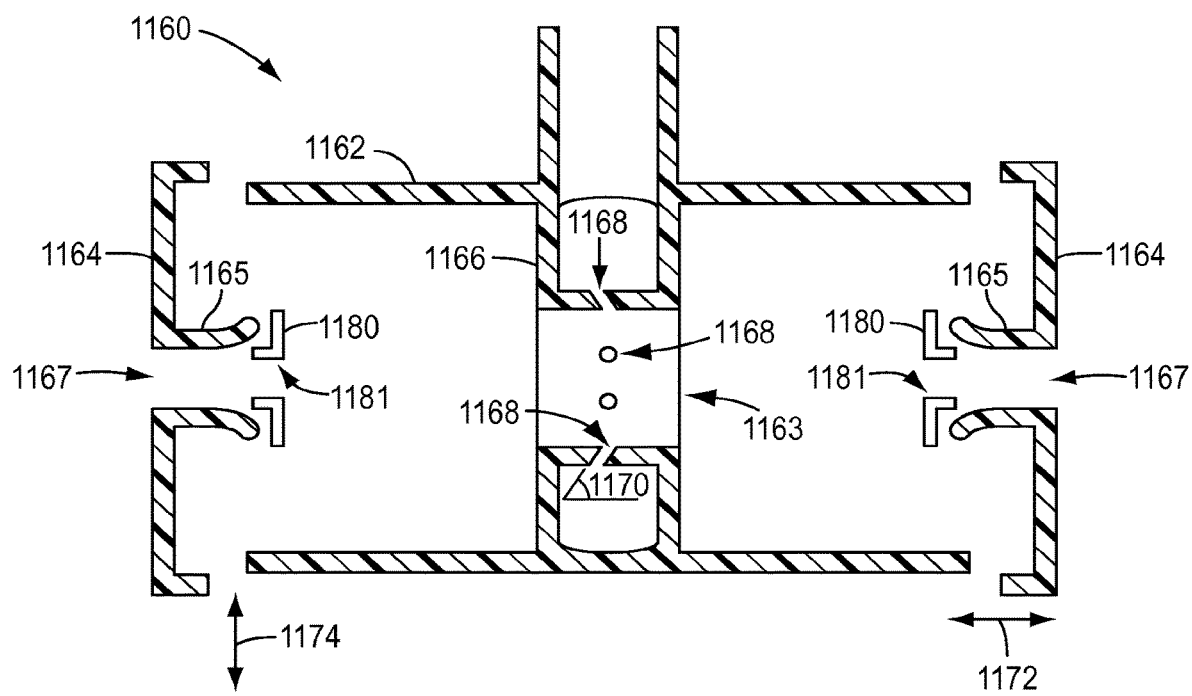
FIG. 23 is a side cross-sectional view of another exemplary embodiment of a cleaning device according to the present disclosure.

Holes 1154 may be positioned at differing angular orientations relative to the central passage 1156 of cleaning device 1140. As shown in the exemplary embodiment of FIG. 21, fluid 1148 directed through holes 1154 may be directed in a substantially radial direction 1158, for example substantially perpendicular to a longitudinal axis of the instrument shaft inserted through central passage 1156. A possible consequence of such a configuration is that fluid 1148 exits cleaning device 1140 through each end piece 1144, which could result in splashing a user of cleaning device 1140. However, holes 1154 of manifold 1150 are not limited to being oriented to direct fluid in a substantially radial direction. Turning to FIG. 23, an exemplary embodiment of a cleaning device 1160 is shown that includes a body 1162 and end pieces 1164. Body 1162 may be configured according to the exemplary embodiment of FIG. 21, except that manifold 1166 includes holes 1168 that are angled in a non-perpendicular direction to the radial direction 1174 of the cleaning device 1160. According to an exemplary embodiment, holes 1168 may be oriented at an angle 1170 that may be, for example, about 20 degrees to about 30 degrees. Angle 1170 for holes 1168 may be selected, for example, to direct a flow of fluid from holes 1168 so that the fluid flows as a radial component and an axial component, with one of the radial and axial components being greater than the other. By directing a portion of the fluid along an axial direction 1172 (or longitudinal axis) towards one of end pieces 1164, the cleaning device 1160 can be utilized with minimal or no splashing by directing an end piece 1164 of cleaning device 1160 through which most or all of the fluid is exiting in a direction away from a user.

As shown in the exemplary embodiments of FIGS. 21 and 23, holes 1154, 1168 may be arranged in a single row or ring along an inner surface of manifold 1150, 1166. However, holes are not limited to such an arrangement and may be arranged in other configurations, such as configuration in which holes are offset (e.g., staggered) along an axial direction of a distributor. Furthermore, holes may be arranged in a plurality of rows or rings along axial direction 1172 on an inner surface of a manifold instead of a single row or ring, as shown in the exemplary embodiments of FIGS. 21 and 23.

The exemplary embodiments of cleaning devices described above may include other features. For instance, a cleaning device 1160 may include members 1180 connected to passages 1165 of end pieces 1164. Members 1180 may be, for example, seals to assist with controlling the flow of fluid within cleaning device 1160. For instance, instead of providing a sealing member 1180 for each end piece 1164, one end piece could include a sealing member 1180 while the other end piece does not to assist a user with directing a spray of fluid out of cleaning device 1160 and away from the user. In another example, members 1180 may be rings that press against a surgical instrument inserted through central openings 1167 of end pieces 1164 to assist with cleaning the surgical instrument by wiping the surgical instrument as the instrument is passed through an end piece 1164. For instance, an inner annular surface 1181 of members 1180 may press against a surgical instrument. In another instance, members 1180 may include bristles (not shown) or other structures, such as along inner annular surface 1181, that press against a surgical instrument to assist with cleaning the instrument.

The cleaning devices of the exemplary embodiments of FIGS. 18-23 may be manufactured according to different methods. A cleaning device may be manufactured, for example, by a three dimensional printing process. For instance, a body of a cleaning device may be printed as a single piece and end pieces may be printed separately. In another example, a cleaning device may be manufactured by a molding process. For instance, a body of a cleaning device may be molded as two piece that are subsequently joined together, such as via ultrasonic welding, with end pieces molded separately. According to an exemplary embodiment, a material used to manufacture a cleaning device may be, for example, a plastic. For instance, a material used to manufacture a cleaning device may be an autoclavable plastic. According to an exemplary embodiment, at least a portion of a cleaning device may be transparent or translucent to permit viewing of an interior of the cleaning device during a cleaning procedure. Further, a lens may be included in a cleaning device to facilitate viewing of the interior of the cleaning device, according to an exemplary embodiment.

Cleaning Fluid Routing Devices

Aside from the cleaning fluid distributors described above with reference to FIGS. 18-23, various exemplary embodiments of the present disclosure contemplate the use of cleaning devices that assist in routing cleaning fluid during cleaning of surgical instruments. Such cleaning fluid routing devices, as will be described in further detail below, can be used when performing cleaning of any of the instruments according to exemplary embodiments herein, and may be used alone or in conjunction with other types of cleaning devices, such as for example the cleaning fluid distributors and/or the proximal flushing manifold described above.

Figure 24:
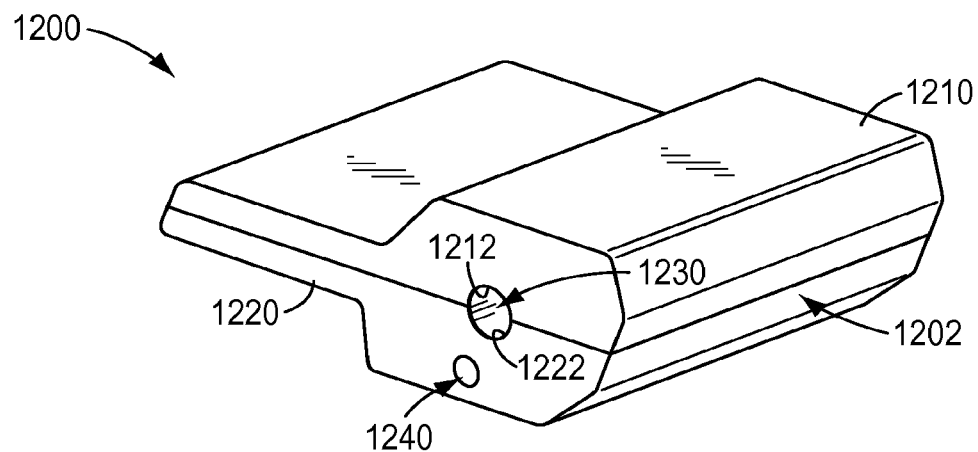
FIG. 24 is a perspective view of yet another exemplary embodiment of a cleaning device in accordance with the present disclosure.
Figure 25:
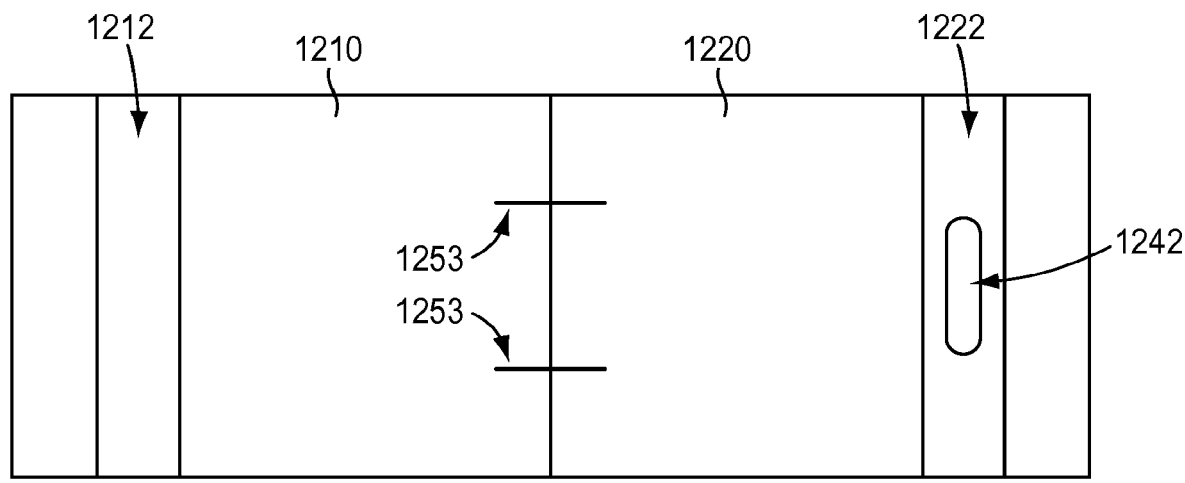
FIG. 25 is a top view of the cleaning device of FIG. 24 in an open position.

Turning to FIG. 24, an exemplary embodiment of a cleaning fluid routing device 1200 is shown that includes a first portion 1210 and a second portion 1220 that are coupled in a manner that permits the device to be moved between a closed position (shown in FIG. 24) and an open position (shown in FIG. 25). According to an exemplary embodiment, first portion 1210 and second portion 1220 may be provided as separate pieces, which may be joined at a parting line 1202, as shown in FIG. 24. For instance, first portion 1210 and second portion 1220 may form halves of cleaning device 1200. According to an exemplary embodiment, first portion 1210 and second portion 1220 may be connected by a hinge 1253 in FIG. 25, which depicts cleaning device 1200 in an opened state. Further, portions 1210, 1220 may include features to fasten portions 1210, 1220 together in a closed position, such as one or more clamping devices. However, although cleaning device 1200 may be provided by a plurality of separate pieces, cleaning device 1200 is not limited to embodiments including plural pieces and may instead consist of a single, one-piece construction.

According to an exemplary embodiment, first portion 1210 and second portion 1220 may respectively include recessed channels 1212, 1222 that together define a passage 1230 through cleaning fluid routing device 1200, as shown in FIGS. 24 and 25. For instance, recessed channels 1212, 1222 of portions 1210, 1220 may be configured, such as to be substantially equal in size so that parting line 1202 bisects passage 1230. Passage 1230 may be configured to receive a surgical instrument inserted through cleaning device 1200, as will be described below. Passage 1230 may include sealing features (not shown), such as, for example, a partial ring of compliant material, such as rubber, located in each recessed channel 1212, 1222 to seal against a shaft of a surgical instrument inserted through passage 1230. According to an exemplary embodiment, sealing features may be configured to reduce a flow of fluid exiting passage 1230 rather than preventing fluid from exiting passage 1230. According to an exemplary embodiment, passage 1230 may have a diameter ranging, for example, from about 0.425 inches to about 0.475 inches.

According to an exemplary embodiment, cleaning device 1200 may include a second passage 1240 configured to receive a cleaning fluid. Further, second passage 1240 may be connected to passage 1230 through which a surgical instrument is inserted. As a result, second passage 1240 may supply fluid to passage 1230, and a surgical instrument inside passage 1230, during a cleaning procedure. A diameter of second passage 1240 may be selected according to a size of fitting used with cleaning device 1200. According to an exemplary embodiment, second passage 1240 may have a diameter of, for example, about 0.380 inches to about 0.420 inches. According to an exemplary embodiment, an aperture 1242 may be provided in passage 1230, an opening of which, for example, is in recessed channel 1222 and is in flow communication with second passage 1240, as shown in FIG. 25. According to another exemplary embodiment, cleaning device 1200 may include a plurality of apertures similar to aperture 1242 in passage 1230 that provides flow communication between passage 1230 and the second passage 1240.

Cleaning device 1200 may be manufactured via, for example, a three-dimensional printing process, a molding process, or other process envisioned by one of ordinary skill in the art. Cleaning device 1200 may comprise, for example, a plastic, such as an autoclavable plastic. According to an exemplary embodiment, cleaning device 1200 may be transparent or translucent, such as to facilitate viewing of passage 1230 during a cleaning procedure.

Figure 26:
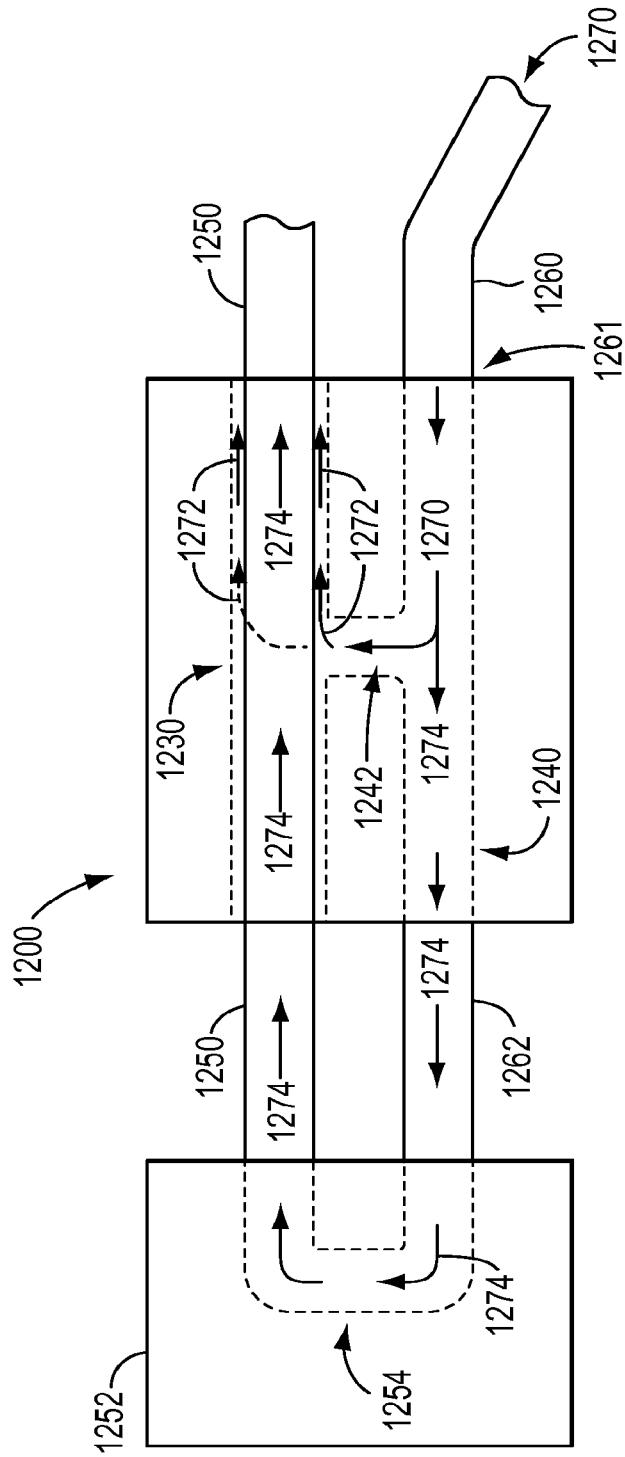
FIG. 26 is a side cross-sectional view of the cleaning device of FIG. 24 during a cleaning procedure for a surgical instrument.

Turning to FIG. 26, a cross-sectional side view is shown of cleaning device 1200 during a cleaning procedure, in which a shaft 1250 of a surgical instrument having a transmission housing 1252 has been inserted through passage 1230 of cleaning device 1200. Housing 1252 may include a flush manifold 1254, for example, configured according to the exemplary embodiment of FIG. 3. Further, a tube 1260 is connected to one end of second passage 1240 to supply a fluid 1270 to second passage 1240. For instance, tube 1260 may be connected to a port 1261 configured to be connected to a fluid supply. Fluid 1270 flows from tube 1260 through passage 1240 to aperture 1242 fluidically connected to passage 1230, at which a first portion 1272 of fluid 1270 may flow through aperture 1242 into passage 1230 and a second portion 1272 of fluid 1272 may continue to flow through second passage 1240. Fluid portion 1272 may flow around an exterior of surgical instrument shaft 1250 within passage 1230 to irrigate the exterior of surgical instrument and then may subsequently exit passage 1230. According to an exemplary embodiment, aperture 1242 may be configured to provide turbulence to fluid portion 1272 flowing around exterior of shaft 1250 within passage 1230. Fluid portion 1274 may flow through second passage 1240, exit from second passage 1240 and flow into a tube 1262 connected to manifold 1254, flow through manifold 1254, and then flow through an interior of surgical instrument shaft 1250, as shown in FIG. 26. Thus, fluid portion 1274 may irrigate an interior of surgical instrument shaft 1250 during a cleaning procedure. Using a cleaning fluid routing device such as that described with reference to FIGS. 24-26 can thus provide a routing mechanism that provides some external cleaning of the inserted instrument shaft as it routes cleaning fluid from a source (such as, e.g., a faucet or the like) to the flushing manifold for interior cleaning of the instrument. According to an exemplary embodiment, surgical instrument shaft 1250 and cleaning device 1200 can remain substantially stationary relative to one another during a cleaning procedure.

In various exemplary embodiments, a desired fluid pressure may be used with the cleaning devices and flush manifolds described above. The desired fluid pressure may be provided, for example, by using a pressure regulator fluidically connected to the source of a fluid used in a cleaning procedure. However, it may be beneficial to provide a mechanism as part of a cleaning device to indicate a fluid pressure, such as when a pressure regulator is not available or is not convenient. According to an exemplary embodiment, the cleaning devices described in the exemplary embodiments of FIGS. 3 and 18-26 may include a fluid pressure indicator to indicate a fluid pressure supplied to the cleaning device. For example, the cleaning device of the exemplary embodiments of FIGS. 3 and 18-27 may include a fluid pressure indicator in the inlet port, such as port 1112 in the exemplary embodiment of FIG. 18, with the fluid pressure indicator being fluidically connected to fluid 1132 supplied to port 1112. In another example, the cleaning device 1200 of the exemplary embodiment of FIGS. 24-26 may include a fluid pressure indicator fluidically connected to passage 1230 and/or passage 1240.

According to an exemplary embodiment, a fluid pressure gauge may qualitatively indicate a fluid pressure. For instance, a fluid pressure gauge may indicate whether a fluid pressure is above a minimum threshold for a desired fluid pressure or whether the fluid pressure below the minimum threshold. According to an exemplary embodiment, the fluid pressure gauge may be a member mounted on a compliant member so that when the fluid pressure gauge is exposed to fluid, the fluid pressure gauge deforms, with the amount of deflection indicating whether the pressure of the fluid exceeds the minimum threshold or not. Thus, the compliant member may be selected to match the desired minimum threshold for fluid pressure. However, a fluid pressure gauge is not limited to a qualitative gauge and may instead be a quantitative gauge that outputs a numerical value for fluid pressure. A quantitative gauge may be, for example, a fluid flow gauge that indicates the amount of flow of a fluid. The compliant member may be, for example, a spring having a known spring constant, an elongated member (e.g., a plastic rod), or other compliant member recognized by one of ordinary skill in the art to provide a fluid flow gauge.

Surgical Instrument Cleaning Methods

Various methods of cleaning a surgical instrument may be contemplated including one or more of the features and devices of the exemplary embodiments described above. The surgical devices and cleaning devices described herein may advantageously permit cleaning of surgical instruments with ordinary water without the use of detergents, although detergents and other cleaning solutions may be used to clean surgical instruments. According to an exemplary embodiment, the water may consist of tap water. According to another exemplary embodiment, the water may comprise distilled water or a water-based solution. A water-based solution may include, for example, an enzymatic detergent, a pH-neutral detergent, or a high-pH detergent. Exemplary detergents include, but are not limited to, for example, Tergazyme® from Alconox, Inc and MediClean Forte from Chemische Fabrik Dr. Weigert GmbH & Co. According to an exemplary embodiment, the water used as a fluid may be at a temperature, for example, that ranges from about 10° C. to about 25° C. According to an exemplary embodiment, the fluid used may be from a supply that is at a pressure ranging, for example, from about 25 psi to about 45 psi. According to another exemplary embodiment, the fluid used may be from a supply that is at a pressure ranging, for example, from about 35 psi to about 40 psi.

A method of cleaning a surgical instrument may include a plurality of steps. A method of cleaning a surgical instrument may include a step of soaking a surgical instrument in a container of water, such as, for example, a sink, for at least about ten minutes. Although a method may include various steps, the steps may be repeated, cancelled, or performed in other orders than those described herein. Further, a surgical instrument cleaned by a cleaning method may be configured according to the exemplary embodiments of FIGS. 2-17. For instance, an instrument may include the manifold described in regard to the exemplary embodiment of FIG. 3 and/or may include an open architecture described in regard to the exemplary embodiments of FIGS. 4-17.

In another step, the surgical instrument may be cleaned by irrigating the surgical instrument, such as by using a cleaning device of the exemplary embodiments of FIGS. 18-23. For instance, a water supply may be connected to port 1112 of the exemplary embodiment of FIGS. 18-20 or the port of any other of the exemplary embodiments of FIGS. 21-23. Further, a surgical instrument may be inserted into and through the cleaning device, such as by inserting the surgical instrument through the central aperture 1122 of an end piece 1120, as shown in the exemplary embodiment of FIG. 19. The surgical instrument may be inserted, for example, along a direction indicated by the visual indicator 1114 shown in the exemplary embodiment of FIG. 19. According to an exemplary embodiment, water may be distributed over a surgical instrument using the cleaning device for a period of, for example, about two minutes. During a cleaning procedure the cleaning device and surgical instrument may be moved relative to one another, such as by sliding the cleaning device and instrument relative to one another along axial direction 1102 and/or rotating the cleaning device and surgical instrument relative to one another in direction 1104, as shown in FIG. 18.

A method of cleaning a surgical instrument may further include cleaning the surgical instrument with the cleaning device 1200 of the exemplary embodiment of FIG. 24-26. For instance, the surgical instrument may be placed within passage 1230 of cleaning device 1200 and tubes 1260, 1262 connected to passage 1240 of cleaning device and manifold 1254 of the surgical instrument so that a fluid portion 1272 may irrigate the exterior of the instrument and a fluid portion 1274 may irrigate an interior of the instrument, as described above in regard to the exemplary embodiment of FIG. 26. According to an exemplary embodiment, a surgical instrument may be irrigated by cleaning device 1200 for a period of, for example, about two minutes. Further, a surgical instrument may be cleaned by the cleaning device of the exemplary embodiments of FIGS. 18-23 and then the cleaning device of the exemplary embodiments of FIGS. 24-26, although other combinations and order of use of the cleaning devices may be used, including using the devices simultaneously on different portions of an instrument shaft.

Additional aspects may be included in a method of cleaning a surgical instrument. For example, the method may further include manually scrubbing an end effector of a surgical instrument. Scrubbing may be accomplished by using, for example, a nylon brush or other scrubbing tool recognized by one of ordinary skill in the art. According to an exemplary embodiment, scrubbing may be conducted, for example, for about two minutes.

Another step that may be included in a method of cleaning a surgical instrument is spraying the surgical instrument with a spray gun. According to an exemplary embodiment, a spray gun is a handheld tool configured to deliver a high pressure jet of water. In an exemplary embodiment, a spray gun, model P/N 80-10-70-38, manufactured and sold by Healthmark Industries, can be used. A spray gun may be used by filling a container, such as a sink, with water, submerging a surgical instrument and the spray gun underwater in the container, and spraying an exterior of the shaft of the surgical instrument. Spraying may be conducted, for example, for about two minutes, such as by moving the spray gun along a longitudinal axis of surgical instrument and/or circumferentially around an exterior of the surgical instrument. Further, when instrument includes an open architecture, such as according to the exemplary embodiments of FIGS. 4-17, fluid ejected from spray gun may penetrate into an interior of the instrument via the open architecture. A step of spraying a surgical instrument with a spray gun may be repeated as necessary.

Another step that may be included in a method of cleaning a surgical instrument is soaking the surgical instrument in a bath of a detergent solution. The detergent solution may be a water based solution including, for example, from about 2% to about 3% Tergazyme® detergent. The bath may be a temperature ranging, for example, from about 45° C. to about 55° C. According to an exemplary embodiment, the soak may be conducted for a period of, for example, about thirty minutes. Once the soak is completed, a rinsing step may be conducted to substantially remove the detergent solution. For instance, irrigating with the cleaning device of the exemplary embodiments of FIGS. 18-23, irrigating with the cleaning device of the exemplary embodiment of FIGS. 24-26, and/or irrigating with the spray gun may be conducted, as described above.

According to an exemplary embodiment, a second soak in a detergent solution may use a detergent solution different than in the first soak. For instance, a second detergent solution soak may use, for example, a water-based solution include about 0.75% to about 1% of Mediclean Forte, which may be a temperature of, for example, about 40° C. to about 45° C. According to an exemplary embodiment, the second soak may be conducted in an ultrasonic tank for a period of, for example, about thirty minutes. Subsequently, the detergent solution may be substantially removed by a rinsing step. For instance, the surgical instrument may be irrigated with the cleaning device of the exemplary embodiments of FIGS. 13-23 and/or irrigated with the cleaning device of the exemplary embodiment of FIGS. 24-26.

According to an exemplary embodiment, a cleaning procedure for a camera device may include the steps described above, except that a camera device need not be irrigated with a cleaning device configured according to the exemplary embodiment of FIGS. 24-26 or with a spray gun. Instead of irrigating a camera device with a cleaning device configured according to the exemplary embodiment of FIGS. 24-26, a camera device may be internally flushed with water by, for example, connecting a hose supplying water to a port 922 for a manifold 920 of the camera device, as shown in the exemplary embodiment of FIG. 3.

Various standards may be used to determine the efficacy of a cleaning procedure. One exemplary standard that may be used is a standard from the Association for the Advancement of Medical Instrumentation (AAMI), AAMI TIR 30:2011, which determines how much material, such as protein or hemoglobin, is left per area of an instrument after a cleaning procedure and whether the amount of material exceeds a given threshold of material per area. Another exemplary standard is ISO 15883 from the International Organization for Standardization, which determines how much material is left after a cleaning procedure and whether the remaining material exceeds a threshold.

The exemplary embodiments and methods described herein have been described as being utilized with surgical instruments for robotic surgical systems. However, the exemplary embodiments and methods described herein may be used with other surgical devices, such as laparoscopic instruments and other manual, hand held instruments.

By providing surgical instruments with the features of the exemplary embodiments described herein, as well as the cleaning devices and methods of the exemplary embodiments described herein, the cleaning of a surgical instrument may be enhanced. In addition, visual inspection of a surgical instrument may be facilitated, such as when the surgical instrument includes an open architecture.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

What is claimed is:

1. A surgical instrument, comprising:
a shaft comprising a distal end, a proximal end, and a wall extending from the distal end to the proximal end, the wall surrounding an interior of the shaft, the shaft having a longitudinal axis extending between the proximal and distal ends;
a transmission housing at the proximal end of the shaft, the shaft being rotatably coupled to the transmission housing;
an actuator in the transmission housing, the actuator being operably coupled to actuate rotation of the shaft;
a port accessible from an exterior of the transmission housing, the port being configured to be fluidically coupled to a fluid supply; and
a manifold in the transmission housing, the manifold comprising an inlet and an outlet, the inlet being in fluid communication with the port, the outlet being in fluid communication with the interior of the shaft,
wherein the shaft is rotatably coupled to the transmission housing, and in response to actuation by the actuator, the shaft rotates about the longitudinal axis of the shaft relative to the transmission housing and the manifold.

2. The surgical instrument of claim 1, further comprising:
an end effector at the distal end of the shaft; and
a second actuator that extends through the manifold at a sealed aperture, the second actuator being operably coupled to move the end effector.

3. The surgical instrument of claim 1, wherein:
the manifold comprises a removable portion; and
an interior of the manifold is accessible on a condition that the removable portion of the manifold is in a removed state.

4. The surgical instrument of claim 1, wherein:
the manifold comprises a removable portion; and
the interior of the shaft is accessible on a condition that the removable portion of the manifold is in a removed state.

5. The surgical instrument of claim 1, wherein the port is configured to be fluidically coupled to the fluid supply via one or more of a tube, a hose, and a faucet.

6. The surgical instrument of claim 1, wherein a direction of fluid flow through the port into the manifold is parallel to the longitudinal axis of the shaft.

7. The surgical instrument of claim 1, wherein the port comprises a locking mechanism configured to maintain a connection between the port and the fluid supply under pressure.

8. The surgical instrument of claim 7, wherein the locking mechanism comprises a locking element biased toward a locking position.

9. The surgical instrument of claim 8, wherein the locking element comprises a plate configured to receive a connection to the fluid supply.

10. The surgical instrument of claim 7, wherein:
the port further comprises a release mechanism configured to release the locking mechanism; and
in a released state of the locking mechanism, the port and the fluid supply are free to be decoupled from each other.

11. The surgical instrument of claim 1, wherein:
at least a portion of the shaft comprises a plurality of openings; and
a fluid communication path is defined from the port, through the manifold, through the interior of the shaft, and through the plurality of openings to an exterior of the shaft.

12. The surgical instrument of claim 11, wherein:
at least one transverse cross-sectional plane through the portion of the shaft intersects multiple openings of the plurality of openings; and
at least one longitudinal cross-sectional plane through the portion of the shaft intersects other multiple openings of the plurality of openings.

13. A surgical instrument, comprising:
a transmission housing;
a shaft comprising a distal end, a proximal end, and a wall surrounding an interior of the shaft, the shaft having a longitudinal axis extending between the proximal and distal ends, the proximal end of the shaft being rotatably coupled to the transmission housing at a rotational coupling;
an actuator in the transmission housing, the actuator being operably coupled to actuate rotation of the shaft;
a fluid port accessible from an exterior of the transmission housing;
a fluid connection locking mechanism coupled to the fluid port; and
a fluid manifold in the transmission housing,
the fluid manifold comprising an inlet and an outlet,
the inlet being in fluid communication with the fluid port,
the outlet being in fluid communication with the interior of the shaft,
wherein, in response to actuation by the actuator, the shaft rotates about the longitudinal axis of the shaft relative to the transmission housing and the fluid manifold.

14. The surgical instrument of claim 13, further comprising:
- an end effector at the distal end of the shaft; and
- a second actuator operably coupled to move the end effector,
- wherein the second actuator extends through the fluid manifold at a sealed aperture.

15. The surgical instrument of claim 13, wherein a direction of fluid flow through the fluid port into the fluid manifold is parallel to the longitudinal axis of the shaft.

16. The surgical instrument of claim 13, wherein the fluid manifold is configured to direct a flow of a cleaning fluid through a 180° turn between the fluid port and the interior of the shaft.

17. The surgical instrument of claim 13, wherein the fluid connection locking mechanism comprises a locking element biased toward a locking position.

18. The surgical instrument of claim 17, wherein the fluid connection locking mechanism further comprises a release configured to move the locking element away from the locking position.

19. The surgical instrument of claim 13, wherein:
- the fluid manifold comprises a removable portion; and
- an interior of the fluid manifold is accessible on a condition that the removable portion of the fluid manifold is in a removed state.

20. The surgical instrument of claim 13, wherein:
- the fluid manifold comprises a removable portion; and
- the interior of the shaft is accessible on a condition that the removable portion of the fluid manifold is in a removed state.

* * * * *